United States Patent
Marfat

(10) Patent No.: US 6,262,040 B1
(45) Date of Patent: Jul. 17, 2001

(54) INDAZOLE DERIVATIVES AND THEIR USE AS INHIBITORS OF PHOSPHODIESTERASE (PDE) TYPE IV AND THE PRODUCTION OF TUMOR NECROSIS FACTOR (TNF)

(75) Inventor: Anthony Marfat, Mystic, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/254,346

(22) PCT Filed: Aug. 25, 1997

(86) PCT No.: PCT/IB97/01023

§ 371 Date: Mar. 4, 1999

§ 102(e) Date: Mar. 4, 1999

(87) PCT Pub. No.: WO98/09961

PCT Pub. Date: Mar. 12, 1998

Related U.S. Application Data

(60) Provisional application No. 60/025,446, filed on Sep. 4, 1996.

(51) Int. Cl.[7] .................. A61K 31/655; A61K 31/41; C07D 231/02; C07D 401/02
(52) U.S. Cl. ................. 514/158; 514/336; 514/337; 514/403; 514/406; 548/361.1; 548/362.1; 548/362.5; 546/275.7
(58) Field of Search ................. 514/158, 403, 514/406, 336, 337, 339; 546/275.7; 548/361.1, 362.1, 362.5

(56) References Cited

U.S. PATENT DOCUMENTS

| | | | |
|---|---|---|---|
| 4,898,863 | * 2/1990 | Brown et al. | 514/235.2 |
| 4,997,844 | * 3/1991 | Bernstein et al. | 548/371 |
| 5,444,038 | 8/1995 | James et al. | 504/253 |
| 5,958,953 | * 9/1999 | Marfat | 514/333 |
| 6,040,329 | * 3/2000 | Marfat | 514/405 |

FOREIGN PATENT DOCUMENTS

| | | | |
|---|---|---|---|
| 381422 A1 | 8/1990 | (EP) | C07D/403/06 |
| 747872 | 4/1956 | (GB) | 2/4 |
| 9117748 | 11/1991 | (WO) | A61K/31/275 |
| 8501980 | 1/1995 | (WO) | C07D/471/04 |
| 9520578 | 8/1995 | (WO) | C07D/213/75 |
| 9522520 | 8/1995 | (WO) | C07C/235/42 |
| 9527692 | 10/1995 | (WO) | C07C/43/23 |

OTHER PUBLICATIONS

*Chemical Abstracts*, 125(13), Sep. 23, 1996, 1122, 167581b.
*Chemical Abstracts*, 107(16), Oct. 19, 1987, 693, 144822v.
*Chemical Abstracts*, 107(15), Oct. 12, 1987, 437, 131065a.
*Chemical Abstracts*, 107(14), Oct. 5, 1987, 582, 124494m.
*Chemical Abstracts*, 102(13), Apr. 1, 1985, 702, 113361m.
*Pharmazie*, 29 ,pp. 685–687 (1974).
Zinnes, et al., *Journal of Medicinal Chemistry*, vol. 16(1), (1973).
Dennler, et al., *Tetrahedron*, vol. 22, pp. 3131to 3141 (1966).
*Chemical Abstracts*, 55(26), Dec. 25, 1961.

* cited by examiner

*Primary Examiner*—Alan L. Rotman
*Assistant Examiner*—Rita Desai
(74) *Attorney, Agent, or Firm*—Peter C. Richardson; Paul H. Ginsburg; Raymond M. Speer

(57) ABSTRACT

The invention relates to compounds of formula (I) and pharmaceutically acceptable salts thereof, wherein R, $R_1$, and $R_2$, are as defined herein. The invention further relates to pharmaceutical compositions containing, and methods of using, the compounds of formula (I), or acceptable salts thereof, for the inhibition of phosphodiesterase (PDE) type IV or the production of tumor necrosis factor (TNF) in a mammal. The invention also relates to intermediates that are useful in the preparation of the compounds of formula (I).

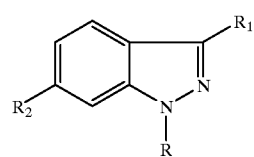

(I)

9 Claims, No Drawings

INDAZOLE DERIVATIVES AND THEIR USE AS INHIBITORS OF PHOSPHODIESTERASE (PDE) TYPE IV AND THE PRODUCTION OF TUMOR NECROSIS FACTOR (TNF)

This application is a continuation of U.S. provisional application Ser. No. 60/025,446, filed Sep. 4, 1996, now abandoned.

This invention relates to novel indazole analogs. The compounds are selective inhibitors of phosphodiesterase (PDE) type IV and the production of tumor necrosis factor (TNF), and as such are useful in the treatment of asthma, arthritis, bronchitis, chronic obstructive airway disease, psoriasis, allergic rhinitis, dermatitis, and other inflammatory diseases, central nervous system disorders such as depression and multi-infarct dementia, AIDS, septic shock and other diseases involving the production of TNF. This invention also relates to a method of using such compounds in the treatment of the foregoing diseases in mammals, especially humans, and to pharmaceutical compositions containing such compounds.

The following co-pending United States provisional patent applications also disclose and claim indazole derivatives that are selective inhibitors of PDE type IV and the production of TNF: U.S. provisional application No. 60/021,072, filed Jun. 27, 1996; U.S. provisional application No. 60/020,385, filed Jun. 25, 1996; and U.S. provisional application No. 60/016,861, filed May 3, 1996. The foregoing co-pending United States provisional patent applications are incorporated herein by reference in their entirety.

Since the recognition that cyclic adenosine phosphate (AMP) is an intracellular second messenger (E. W. Sutherland, and T. W. Rall, *Pharmacol. Rev.*, 12, 265, (1960)), inhibition of the phosphodiesterases has been a target for modulation and, accordingly, therapeutic intervention in a range of disease processes. More recently, distinct classes of PDE have been recognized (J. A. Beavo et al., *Trends in Pharm. Sci.* (TIPS), 11, 150, (1990)), and their selective inhibition has led to improved drug therapy (C. D. Nicholson, M. S. Hahid, *TIPS*, 12, 19, (1991)). More particularly, it has been recognized that inhibition of PDE type IV can lead to inhibition of inflammatory mediator release (M. W. Verghese et al., *J. Mol. Cell Cardiol.*, 12 (Suppl. II), S 61, (1989)) and airway smooth muscle relaxation (T. J. Torphy in "Directions for New Anti-Asthma Drugs," eds S. R. O'Donnell and C. G. A. Persson, 1988, 37 Birkhauser-Verlag). Thus, compounds that inhibit PDE type IV, but which have poor activity against other PDE types, would inhibit the release of inflammatory mediators and relax airway smooth muscle without causing cardiovascular effects or antiplatelet effects. It has also been disclosed that PDE IV inhibitors are useful in the treatment of diabetes insipidus (Kidney Int. 37:362, 1990; Kidney Int. 35:494) and central nervous system disorders such as depression and mult-infarct dementia (PCT international application WO 92/19594 (published Nov. 12, 1992)).

TNF is recognized to be involved in many infectious and auto-immune diseases (W. Friers, *Fed. of Euro. Bio. Soc.* (FEBS) Letters, 285, 199, (1991)). Furthermore, it has been shown that TNF is the prime mediator of the inflammatory response seen in sepsis and septic shock (C. E. Spooner et al., Clinical Immunology and Immunopathology, 62, S11, (1992)).

SUMMARY OF THE INVENTION

The present invention relates to compounds of the formula I

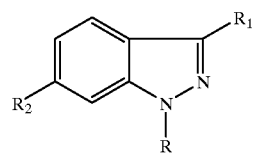

and to pharmaceutically acceptable salts thereof, wherein:

R is H, $C_1$–$C_9$ alkyl, -$(CH_2)_m$(5 to 10 membered heterocyclyl) wherein m is 0 to 2, ($C_1$–$C_6$ alkoxy)$C_1$–$C_6$ alkyl, $C_2$–$C_6$ alkenyl, or -$(Z_1(_b(Z_2)_c(C_6$–$C_{10}$ aryl) wherein b and c are independently 0 or 1, $Z_1$ is $C_1$–$C_6$ alkylene or $C_2$–$C_6$ alkenylene, and $Z_2$ is O, S, $SO_2$, or $NR_{12}$, and wherein said R groups are optionally substituted by 1 to 3 substituents independently selected from the group consisting of halo, hydroxy, $C_1$–$C_6$ alkyl, $C_2$–$C_5$ alkenyl, $C_1$–$C_6$ alkoxy, trifluoromethyl, nitro, —$CO_2R_{12}$, —$C(O)NR_{12}R_{13}$, —$NR_{12}R_{13}$ and —$SO_2NR_{12}R_{13}$;

$R_1$ is H, $C_1$–$C_9$ alkyl, $C_2$–$C_3$ alkenyl, or phenyl, wherein said alkyl, alkenyl and phenyl $R_1$ groups are optionally substituted by 1 to 3 substituents independently selected from the group consisting of methyl, ethyl, trifluoromethyl, and halo;

$R_2$ is $R_{19}$, —$C(O)NR_{12}(CHR_{12})_mC(O)NR_{12}O(CH_2)_q$($C_6$–$C_{10}$ aryl), —$C(=NR_{32})NH(CH_2)_p(C_6$–$C_{10}$ aryl), —$C(O)NR_6(CHR_{12})_mC(O)NR_{12}(CH_2)_pOR_{12}$, —$C(O)NR_{12}(CHR_{12})_mS(C_1$–$C_4$ alkyl), —$C(=NOC(O)R_{25})R_{26}$, —$CR_{17}R_{18}CHR_{28}NR_9SO_2(CH_2)_pA$, —$CR_{17}R_{18}CHR_{28}NR_9P(O)(OR_{12})C(O)(C_1$–$C_4$ alkyl), —$CR_{17}R_{18}CHR_{28}NR_9P(O)(C_1$–$C_4$ alkoxy)_2$, —$Z_3$-$R_7$, or -$(CR_{17}R_{18})_mNR_9(C(O))_qR_{10}$ wherein p is 0 to 2, m is 1 to 6, and q is 1 or 2; or $R_2$ is

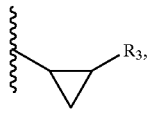

(Ia)

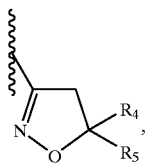

(Ib)

(Ic)

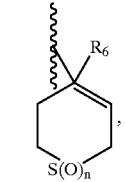

(Id)

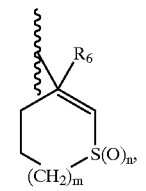

-continued

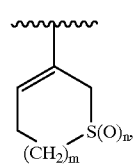
(Ie)

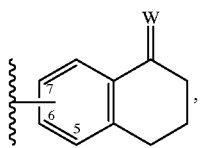
(If)

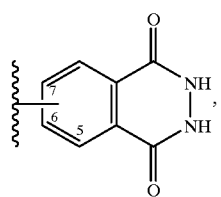
(Ig)

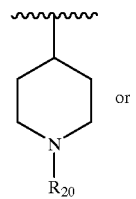
or
(Ih)

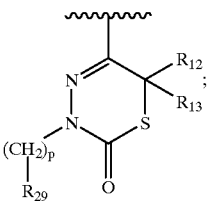
(Ii)

wherein in said formulas (Ia)–(Ii), the structures of formulas (If) and (Ig) are attached to formula I at carbons 5, 6, or 7 of said formulas (If) and (Ig), the dashed line in formulas (Ic) and (Id) indicates a single bond or double bond, except $R_6$ is absent in formulas (Ic) and (Id) where said dashed line indicates a double bond, n is 0 to 2, p is 0 to 6, and m is 0 or 1;

$R_3$ is —C(O)N(CH$_3$)(OCH$_3$) or -(CH$_2$)$_n$OH wherein n is 0 to 4;

$R_4$ and $R_5$ are independently selected from the group consisting of H, ethyl, —CO$_2$H and —C(O)NHOH;

$R_6$ is H, cyano, hydroxy, $C_1$–$C_6$ alkyl, $C_1$–$C_6$ alkoxy, —OC(O)($C_1$–$C_6$ alkyl) or —OC(O)($C_6$–$C_{10}$ aryl);

$R_7$ is $C_6$–$C_{10}$ aryl or 5 to 10 membered heterocyclyl, wherein said $R_7$ groups are optionally substituted by 1 to 3 substituents independently selected from halo, trifluoromethyl, cyano, nitro, —CO$_2$R$_{12}$, $C_1$–$C_4$ alkoxy, —OC(O)($C_1$–$C_4$ alkyl), —NR$_{12}$C(O)($C_1$–$C_4$ alkyl), —C(O)NH$_2$, —C(O)NHOH, —C(O)O($C_1$–$C_4$ alkyl), $C_1$–$C_4$ alkyl, —S(O)$_n$R$_{12}$ wherein n is 0 to 2, benzoyl, —NR$_{12}$R$_{13}$, —OR$_{12}$, $C_1$–$C_6$ alkanoyl, —Y$_1$-($C_6$–$C_{10}$ aryl), —C(O)O ($C_6$–$C_{10}$ aryl), —NH($C_6$C$_{10}$ aryl), —C(O)NH($C_6$C$_{10}$ aryl), —C(O)NR$_{12}$O(CH$_2$)$_n$($C_6$–$C_{10}$ aryl) wherein n is 1 to 3, and —SO$_2$NH($C_6$C$_{10}$ aryl);

$R_8$ is H, $C_1$–$C_6$ alkyl, or -(CH$_2$)$_n$($C_6$–$C_{10}$ aryl) wherein n is 0 to 4;

$R_9$ is H, —OR$_{12}$, -(CH$_2$)$_m$A or —CH$_2$O(CH$_2$)$_m$A wherein m is 0 to 2;

$R_{10}$ is $C_1$–$C_4$ alkyl, —OR$_{12}$, —CR$_{12}$R$_{13}$OR$_{12}$, —CR$_{12}$R$_{13}$NR$_{12}$R$_{13}$, —CR$_{12}$(OR$_{13}$)CR$_{12}$R$_{13}$OR$_{12}$, 2,2-dimethyl-1,3-dioxolan-4-yl, —NR$_{12}$C(O)NR$_{12}$R$_{13}$, —S(CR$_{12}$R$_{13}$)$_n$CH$_3$ wherein n is 0 to 5, —NR$_{12}$(CH$_2$)$_q$ (pyridyl) wherein q is 0 or 1, —P(O)($C_1$–$C_4$ alkoxy)$_2$, —NR$_{12}$R$_{13}$, —NR$_{12}$OR$_{13}$, —NR$_{12}$NR$_{13}$R$_{11}$, —NR$_{12}$CH$_2$R$_{14}$, —OCH$_2$NR$_{12}$C(O)R$_{14}$, —OCH$_2$C(O) NR$_{15}$R$_{16}$, —OCHR$_{12}$OC(O)($C_1$–$C_4$ alkyl), —OCHR$_{12}$C(O) ($C_1$–$C_3$ alkoxy), —O(CH$_2$)$_m$R$_{11}$, or —NR$_{12}$(CH$_2$)$_m$R$_{11}$ wherein m is 0 to 2;

$R_{11}$ is H or A;

each $R_{12}$ and $R_{13}$ is independently H or $C_1$–$C_4$ alkyl;

$R_{14}$ is methyl or phenyl;

$R_{15}$ is H, methyl, ethyl, or —CH$_2$CH$_2$OH;

$R_{16}$ is H, methyl, ethyl, —CH$_2$C(O)NH$_2$, or —CH$_2$CH$_2$OH;

each $R_{17}$ is independently H, hydroxy, cyano, halo, $C_1$–$C_3$ alkyl, $C_1$–$C_3$ alkoxy, —NR$_{12}$R$_{13}$, —C(O)OR$_{12}$, —C(O)R$_{12}$, —CH=CR$_{12}$R$_{13}$, —C=CR$_{12}$, —CH$_2$NR$_{12}$R$_{13}$, —CH$_2$OR$_{12}$, —C(O)NR$_{12}$R$_{13}$, —C(Y$_5$)H, or —CH$_2$NR$_{12}$C(O)C(O)NR$_{12}$R$_{13}$, provided that when $R_{17}$ is hydroxy then $R_{18}$ is H or $C_1$–$C_4$ alkyl;

each $R_{18}$ is independently H, fluoro, cyano, or $C_1$–$C_4$ alkyl, wherein said methyl is optionally substituted by 1 to 3 fluoro substituents;

or $R_{17}$ and $R_{18}$ are taken together to form an oxo (=O) moiety;

$R_{19}$ is phenyl, naphthyl, pyrrolyl, furanyl, thienyl, oxazolyl, pyridinyl, pyrimidinyl, pyridazinyl, quinolinyl, isoquinolinyl, 5,6,7,8-tetrahydroquinolinyl, or 5,6,7,8-tetrahydroisoquinolinyl, wherein said $R_{19}$ groups, except said phenyl, are optionally substituted by 1 to 3 $R_{23}$ substituents, and wherein said phenyl $R_{19}$ group is optionally substituted by 1 to 3 substituents independently selected from $R_{23}$ and $R_{24}$;

$R_{20}$ is —C(O)R$_{21}$, —C(O)C(O)R$_{21}$, —C(O)C(Y$_2$)C(O) R$_{21}$ or

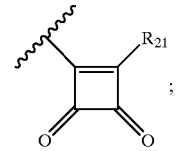

$R_{21}$ is H, —OR$_{22}$, —NHR$_{22}$, —NHOH, —NHNH$_2$, -(CH$_2$)$_n$Y$_3$(phenyl) or -(CH$_2$)$_n$Y$_3$(pyridyl) wherein n is 0 to 4;

$R_{22}$ is H, $C_1$–$C_8$ alkyl, -(CH$_2$)$_n$Y$_3$(phenyl) or -(CH$_2$)$_n$Y$_3$ (pyridyl) wherein n is 0 to 4;

each $R_{23}$ is independently halo, $C_1$–$C_6$ alkyl, $C_1$–$C_7$ alkoxy, $C_2$–$C_6$ alkylenedioxy, trifluoromethyl, —NR$_{12}$R$_{13}$, nitro, —C(NR$_{12}$)NR$_{12}$R$_{13}$, —C(O)NR$_{12}$R$_{13}$C(O)R$_{12}$, —C(NOR$_{12}$)R$_{13}$, —C(NCN)NR$_{12}$R$_{13}$, —C(NCN)SR$_{12}$, -(CH$_2$)$_m$(CN) wherein m is 0 to 3, hydroxy, —C(O)R$_{12}$, —C(O)NR$_{12}$OR$_{13}$, —C(O)NR$_{12}$NR$_{12}$R$_{13}$, —OC(O)NR$_{12}$R$_{13}$, —NR$_{12}$C(O)R$_{12}$, —C(O)C(O)NR$_{12}$R$_{13}$, —CO$_2$R$_{12}$, —SO$_2$R$_{12}$, —SO$_2$NR$_{12}$R$_{13}$, —C(O)NR$_{12}$R$_{13}$, —NR$_{12}$SO$_2$R$_{13}$, or —NR$_{12}$C(O)NR$_{12}$R$_{13}$;

each $R_{24}$ is independently imidazolyl, pyrazolyl, triazolyl, tetrazolyl oxazolyl, isoxazolyl, oxadiazolyl, thiadiazolyl, thiazolyl, oxazolidinyl, thiazolidinyl, or imidazolidinyl, wherein each of the foregoing $R_{24}$ substituents is optionally substituted by 1 to 3 $R_{23}$ substituents;

$R_{25}$ is —NR$_{12}$R$_{13}$, —NH($C_6$–$C_{10}$ aryl), $C_1$–$C_6$ alkoxy, or $C_6$–$C_{10}$ aryloxy;

$R_{26}$ is H, $C_1$–$C_6$ alkyl or -$(CH_2)_m Y_4$(phenyl) wherein m is 0 to 4 and the phenyl moiety of said -$(CH_2)_m Y_4$(phenyl) $R_{26}$ group is optionally substituted by halo, —$OR_{12}$, $C_1$–$C_6$ alkanoyloxy, $C_6$–$C_{10}$ aryloxy, —$NR_{12}R_{13}$, —$NH(C_6$–$C_{10}$ aryl), or —$NHC(O)(C_1$–$C_4$ alkyl);

each $R_{27}$ is independently halo, —$(CH_2)_p NR_{12}C(O)CH_3$ wherein p is 1 to 5, nitro, cyano, —$NR_{12}R_{13}$, —$CO_2R_{12}$, —$OR_{12}$, —$C(Y_1)NR_{12}R_{13}$, —$NR_{12}C(NCN)S(C_1$–$C_3$ alkyl), —$NR_{12}C(NCN)NR_{12}R_{13}$, —$NR_{12}C(O)NR_{12}R_{13}$, —$NR_{12}C(O)C(O)NR_{12}R_{13}$, —$C(=NR_{12})NR_{12}R_{13}$, —$S(O)_m CH_3$ wherein m is 0 to 2, —$C(=NR_{12})S(C_1$–$C_3$ alkyl), —$NR_{12}SO_2(C_1$–$C_3$ alkyl), —$OC(O)R_{12}$, —$OC(O)NR_{12}R_{13}$, —$NR_{12}SO_2CF_3$, —$NR_{12}C(O)C(O)OR_{12}$, —$NR_{12}C(O)R_{12}$, —$NR_{12}C(O)OR_{12}$, imidazolyl, thiazolyl, oxazolyl, pyrazolyl, triazolyl, or tetrazolyl;

$R_{28}$ is H, fluoro, cyano, or $C_1$–$C_2$ alkyl, wherein said alkyl is optionally substituted by 1 to 3 substituents independently selected from halo, —$C(O)NR_{12}R_{13}$, and —$C(O)OR_{12}$;

$R_{29}$ is phenyl optionally substituted by 1 or 2 substituents independently selected from —$NR_{12}R_{13}$, nitro, halo, —$OR_{12}$, —$NHR_{30}$, —$NR_{30}R_{31}$, and —$C(O)OR_{12}$;

each $R_{30}$ and $R_{31}$ is independently $C_1$–$C_6$ alkyl or $C_2$–$C_6$ alkenyl;

$R_{32}$ is pyridin-4-yl optionally substituted by 1 or 2 substituents independently selected from halo and $C_1$–$C_4$ alkyl;

each A is independently $C_1$–$C_6$ alkyl, pyridyl, morpholinyl, piperidinyl, imidazolyl, thienyl, pyrimidyl, thiazolyl, triazolyl, quinolinyl, phenyl, or naphthyl, wherein the foregoing A groups are optionally substituted with 1 to 3 $R_{27}$ substitutents, or A is -$(CH_2)_q S(C_1$–$C_4$ alkyl) wherein q is 1 or 2;

W is O, NOH, $NNH_2$, $NOC(O)CH_3$, or $NNHC(O)CH_3$;

$Y_1$ is O or S;

$Y_2$ is O, NOH or $H_2$;

$Y_3$ is a bond or —CH=CH—;

$Y_4$ is a bond, O, S, or —NH—;

$Y_5$ is O, $NR_{12}$, $NOR_{12}$, NCN, $C(CN)_2$, $CR_{12}NO_2$, $CR_{12}C(O)OR_{12}$, $CR_{12}C(O)NR_{12}R_{13}$, $C(CN)NO_2$, $C(CN)C(O)OR_{12}$ or $C(CN)C(O)NR_{12}R_{13}$; and, $Z_3$ is —$NR_{12}$-, -$(CH_2)_m$-, —$CH_2C(O)NH$—, —$NHCH_2C(O)$-, —$CH_2C(Y_1)CH_2$-, —CH=CH—, —C≡C—, —CH$(Y_1H)$-, —$C(Y_1)$, —$CH_2C(Y_1)$-, —$C(Y_1)CH_2$-, —$C(Y_1)C(Y_1)$-, —$CH_2NR_{12}$-, —$CH_2$-$Y_1$-, —$C(Y_1)NR_6(CHR_{12})_n$-, —$NR_6C(Y_1)(CHR_{12})_n$-, —$NHCH_2$-, —$Y_1$-$CH_2$-, —$SOCH_2$-, —$CH_2SO$—, —$SO_2CH_2$-, —$CH_2SO_2$-, —$OC(Y_1)$-, —N=N—, —$NHSO_2$-, —$SO_2NH$-, —$C(Y_1)C(Y_1)NH$—, —$NHC(O)O$—, —$OC(O)NH$— or —$NHC(O)NH$—, wherein in said $Z_3$ moieties n is 0 to 4 and m is 1 to 3.

The present invention also relates to compounds of the formula

XXXX

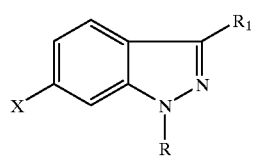

and to pharmaceutically acceptable salts thereof, wherein R and $R_1$ are as defined above and X is —C(O)Cl. The compounds covered by the above formula are intermediates that are useful in the preparation of the compounds of formula I.

Specific compounds of formula I include those wherein $R_2$ is —$Z_3$-$R_7$ wherein $Z_3$ is —$C(Y_1)NH$—, —$C(O)CH_2$-, —$NHC(Y_1)$-, —$Y_1$-$CH_2$-, —OC(O)-, —CH=CH—, or —$C(Y_1)C(Y_1)$-, and $R_7$ is an optionally substituted aryl or heteroaryl group selected from phenyl, pyridyl, pyrazinyl, thienyl, pyrimidinyl, 2,4-dioxopyrimidin-5-yl, isoxazolyl, isothiazolyl, pyridazinyl, and 1,2,4-triazinyl. More specifically, $R_7$ is substituted phenyl, 2,6-dihalo-substituted phenyl, or 3,5-dihalo-pyrid-4-yl.

Other specific compounds of formula I include those wherein $R_2$ is —$Z_3$-$R_7$ wherein $Z_3$ is —$C(O)NH(CH_2)_n$- or —$NHC(O)(CH_2)_n$-, wherein n is 0 or 1, and $R_7$ is phenyl or pyridyl optionally substituted by 1 to 3 substituents independently selected from halo, nitro, trifluoromethyl, —$CO_2CH_3$, methyl, methoxy, and —$C(O)NH_2$.

Other specific compounds of formula I include those wherein $R_2$ is —$Z_3R_7$ wherein $Z_3$ is —C(O)NH— and $R_7$ is phenyl or pyridyl optionally substituted by 1 to 3 substituents independently selected from halo, $C_1$–$C_4$ alkyl, $C_1$–$C_4$ alkoxy, cyano, carboxy and —$OC(O)(C_1$–$C_4$ alkyl).

Other specific compounds of formula I include those wherein $R_2$ is $R_{19}$ wherein $R_{19}$ is optionally substituted pyrimidinyl or optionally substituted pyridazinyl.

Other specific compounds of formula I include those wherein $R_2$ is a substitutent of formula (Ih) wherein $R_{20}$ is —$C(O)R_{21}$, —$C(O)C(O)R_{21}$, or

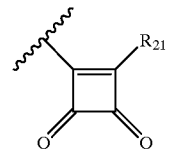

wherein $R_{21}$ is —$OR_{22}$, —$NHR_{22}$, or —NHOH, and $R_{22}$ is H, $C_1$–$C_3$ alkyl, benzyl or pyridylmethyl.

Other specific compounds of formula I include those wherein $R_2$ is phenyl substituted by $R_{24}$ wherein said $R_{24}$ is oxadiazolyl, thiadiazolyl or tetrazolyl wherein said $R_{24}$ groups are optionally substituted by $C_1$–$C_2$ alkyl, or wherein $R_2$ is phenyl substituted by cyanomethyl, hyroxy or formyl.

Other specific compounds of formula I include those wherein $R_2$ is —$Z_3$-$R_7$ wherein $Z_3$ is —$C(Y_1)NH$—, and $R_7$ is phenyl, pyrazinyl, pyrimidinyl, isoxazolyl, or pyridyl, wherein each of said $R_7$ groups is optionally substituted by 1 to 3 substituents independently selected from halo, methoxycarbonyl, trifluoromethyl, benzoyl, acetyl, dimethylamino, hydroxy, nitro, methyl, cyano, methylsulphonyl, and methylthio.

Other specific compounds of formual I include those wherein $R_2$ is —$C(=NOC(O)R_{25})R_{26}$ wherein $R_{25}$ is amino and $R_{26}$ is H, $C_1$–$C_3$ alkyl or -$(CH_2)_m$(phenyl) wherein m is 1 to 4 and said phenyl moiety is optionally substituted by halo, hydroxy, acetoxy, amino or acetamido.

Other specific compounds of formual I include those wherein $R_2$ is -$(CR_{17}R_{16})_m NR_6(C(O))_q R_{10}$ wherein m is 2, q is 2, each $R_{17}$ is independently H, cyano or methyl, each $R_{18}$ is independently H or methyl, $R_9$ is H or methyl, and $R_{10}$ is amino, hyroxy, methoxy or hydroxyamino.

Other specific compounds of formula I include those wherein $R_2$ is -$(CR_{17}R_{18})_m NR_9(C(O))_q R_{10}$ wherein m is 2, q is 1, each $R_{17}$ is independently H, —$C(O)NH_2$, —C=CH, cyano, formyl, hydroxymethyl, or trifluoromethyl, each $R_{18}$ is independently H or cyano, and $R_{10}$ is $C_1$–$C_4$ alkyl.

Other specific compounds of formual I include those wherein $R_2$ is a substitutent of formula (Ic), (Id) or (Ie), wherein, in formulas (Ic) and (Id), $R_6$ is H, hydroxy, $C_1$–$C_4$ alkyl or $C_1$–$C_4$ alkoxy.

Other specific compounds of formual I include those wherein $R_2$ is —$C(O)NR_8(CHR_{12})_m C(O)NR_{12}(CH_2)_p OR_{12}$ or —C(O)NR$_{12}$(CHR$_{12}$)$_m$S(C$_1$–C$_4$ alkyl), wherein R$_8$, R$_{12}$, m and p are as defined above.

Specific compounds of formual I include those selected from the group consisting of:
1-Cyclopentyl-3-ethyl-1H-indazole-6-carboxylic acid (3,5-dichloro-pyridin-4-yl)-amide;
1-Cyclopentyl-3-ethyl-1H-indazole-6-carboxylic acid (2,6-dichloro-phenyl)-amide;
1-Cyclobutyl-3-ethyl-1H-indazole-6-carboxylic acid (3,5-dichloro-pyridin-4-yl)-amide;
3-Ethyl-1-isopropyl-1H-indazole-6-carboxylic acid (3,5-dichloro-pyridin-4-yl)-amide;
1-Cyclopropylmethyl-3-ethyl-1H-indazole-6-carboxylic acid (3,5-dichloro-pyridin-4-yl)-amide;
1-Cyclohexyl-3-ethyl-1H-indazole-6-carboxylic acid (3,5-dichloro-pyridin-4yl)-amide;
3-Ethyl-1(4-fluoro-phenyl)-1H-indazole-6-carboxylic acid (3,5-dichloro-pyridin-4-yl)-amide;
1-Cyclopentyl-3-ethyl-1H-indazole-6-crboxylic acid hyroxycarbamoylmethyl-amide;
1-Cyclopentyl-3-ethyl-1H-indazole-6-carboxylic acid (2-methylsulfanyl-ethyl)-amide;
1-Cyclopentyl-3-ethyl-1H-indazole-6-carboxylic acid hydroxycarbamoylmethyl-methyl amide;
S-1-Cyclopentyl-3-ethyl-1H-indazole-6-carboxylic acid (1-benzyloxycarbamoyl-ethyl)-amide;
R-1-Cyclopentyl-3-ethyl-1H-indazole-6-carboxylic acid (1-hyroxycarbamoyl-ethyl)-amide; 1-Cyclopentyl-3-ethyl-6-thiophen-2-yl-1H-indazole; 1-Cyclopentyl-3-ethyl-6-phenyl-1H-indazole; and the pharmaceutically acceptable salts of the foregoing compounds.

The present invention further relates to a pharmaceutical composition for the inhibition of phosphodiesterase (PDE) type IV or the production of tumor necrosis factor (TNF) comprising a pharmaceutically effective amount of a compound according to formula I, as defined above, or a pharmaceutically acceptable salt thereof, and a pharmaceutically acceptable carrier.

The present invention further relates to a method for the inhibition of phosphodiesterase (PDE) type IV or the production of tumor necrosis factor (TNF) by administering to a patient an effective amount of a compound according to formula I, as defined above, or a pharmaceutically acceptable salt thereof.

The present invention further relates to a pharmaceutical composition for the prevention or treatment of asthma, joint inflammation, rheumatoid arthritis, gouty arthritis, rheumatoid spondylitis, osteoarthritis, and other arthritic conditions; sepsis, septic shock, endotoxic shock, gram negative sepsis, toxic shock syndrome, acute respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secodary to infection or malignancy, cachexia secondary to human acquired immune deficiency syndrome (AIDS), AIDS, HIV, ARC (AIDS related complex), keloid formation, scar tissue formation, Crohn's disease, ulcerative colitis, pyresis, multiple sclerosis, type 1 diabetes mellitus, diabetes insipidus, autoimmune diabetes, systemic lupus erythematosis, bronchitis, chronic obstructive airway disease, psoriasis, Bechet's disease, anaphylactoid purpura nephritis, chronic glomerulonephritis, inflammatory bowel disease, leukemia, allergic rhinitis, dermatitis, depression or multi-infarct dementia, comprising a pharmaceutically effective amount of a compound according to formual I, as defined above, or a pharmaceutically acceptable salt, thereof together with a pharmaceutically acceptable carrier.

The present invention further relates to a method of treating or preventing the foregoing specific diseases and conditions by administering to a patient an effective amount of a compound according to formula I, as defined above, or a pharmaceutically acceptable salt thereof.

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. It is to be understood that where cyclic moieties are intended, at least three carbons in said alkyl must be present. Such cyclic moieties include cyclopropyl, cyclobutyl, cyclopentyl, cyclohexyl and cycloheptyl.

The term "alkoxy", as used herein, unless otherwise indicated, includes —O-alkyl groups wherein alkyl is as defined above.

The term "alkanoyl", as used herein, unless otherwise indicated, includes —C(O)— alkyl groups wherein alkyl is as defined above.

The term "aryl", as used herein, unless otherwise indicated, includes an organic radical derived from an aromatic hydrocarbon by removal of one hydrogen, such as phenyl or naphthyl.

The term "5 to 10 membered heterocyclyl", as used herein, unless otherwise indicated, includes aromatic and non-aromatic heterocyclic groups containing one or more heteroatoms each selected from O, S and N, wherein each heterocyclic group has from 5 to 10 atoms in its ring system. The heterocyclic groups include benzo-fused ring systems and ring systems substituted with one or more oxo moieties. An example of a 5 membered heterocyclic group is thiazolyl, and an example of a 10 membered heterocyclic group is quinolinyl. Examples of non-aromatic heterocyclic groups are pyrrolidinyl, piperidino, morpholino, thiomorpholino and piperazinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include benzimidazolyl.

The term "heteroaryl", as used herein, unless otherwise indicated, includes aromatic heterocyclic groups wherein heterocyclic is as defined above.

The phrase "pharmaceutically acceptable salt(s)", as used herein, unless otherwise indicated, includes salts of acidic or basic groups which may be present in the compounds of formula I.

Certain compounds of formula I may have asymmetric centers and therefore exist in different enantiomeric forms. This invention relates to the use of all optical isomers and stereoisomers of the compounds of formula I and mixtures thereof. The compounds of formula I may also exist as tautomers. This invention relates to the use of all such tautomers and mixtures thereof.

DETAILED DESCRIPTION OF THE INVENTION

The following reaction Schemes 1–8 illustrate the preparation of the compounds of the present invention. In the following Schemes, unless otherwise indicated, R, R$_1$, R$_7$, R$_8$, and R$_{12}$ are as defined above. In the following Schemes, "Me" means methyl and "Ph" means phenyl.

Scheme 1
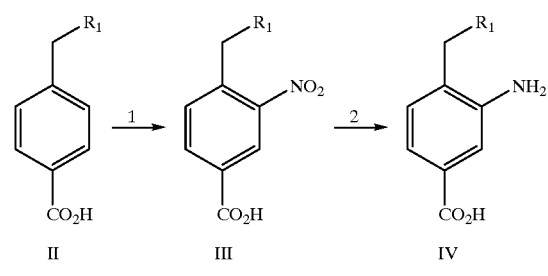
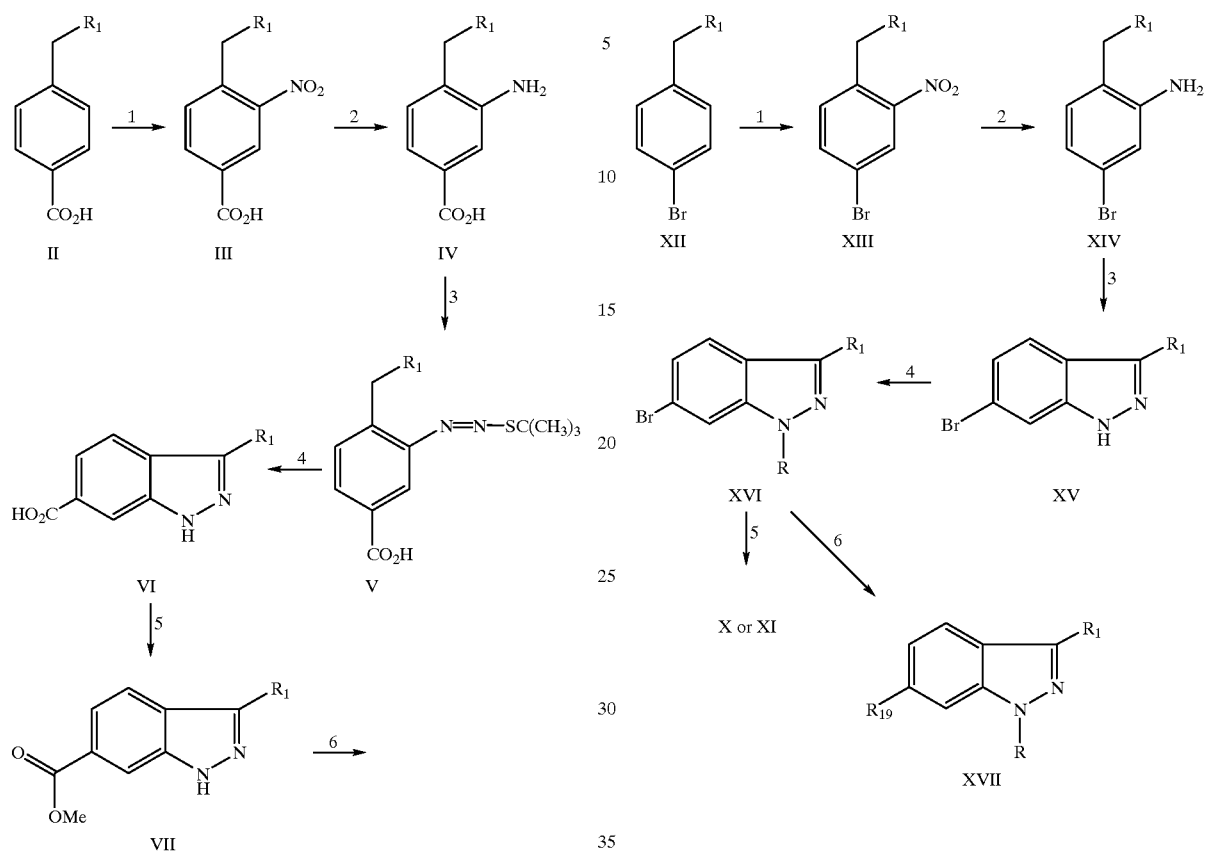
Scheme 2
Scheme 3
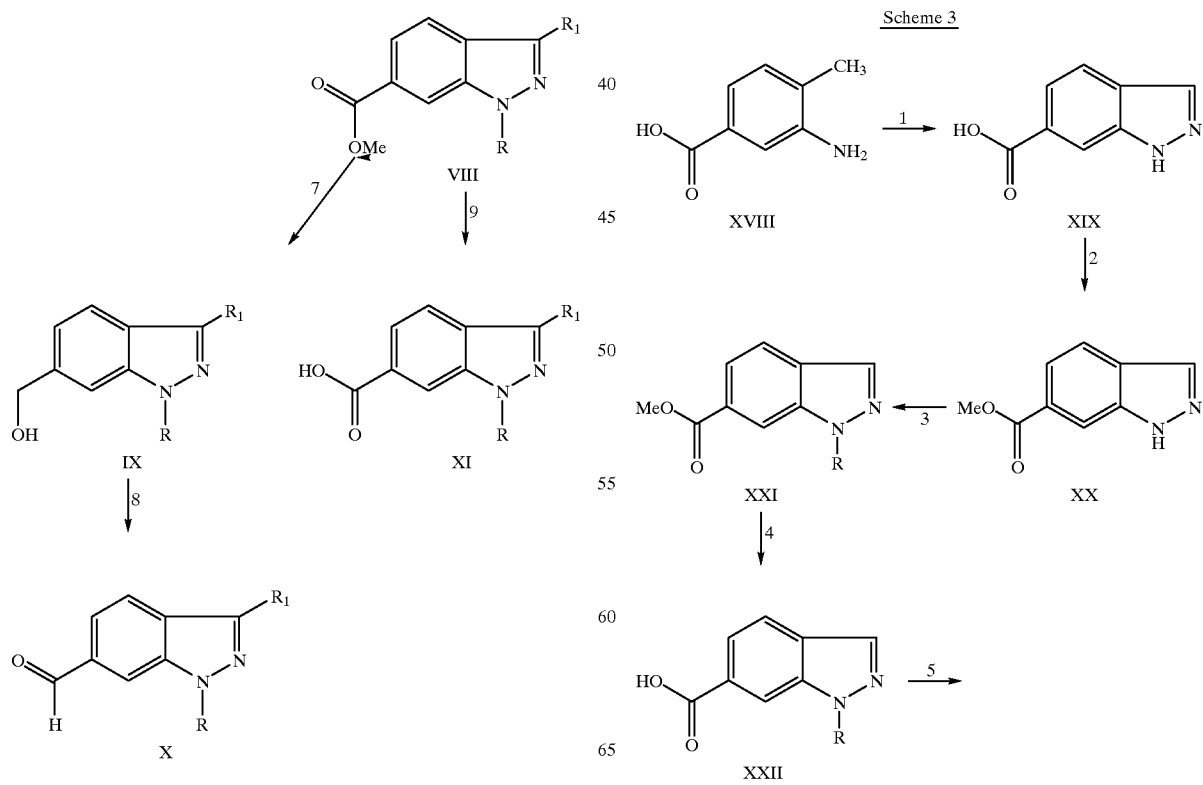

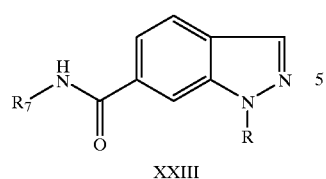
XXIII
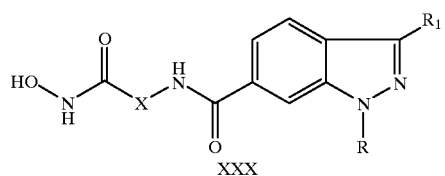
XXX
Scheme 4
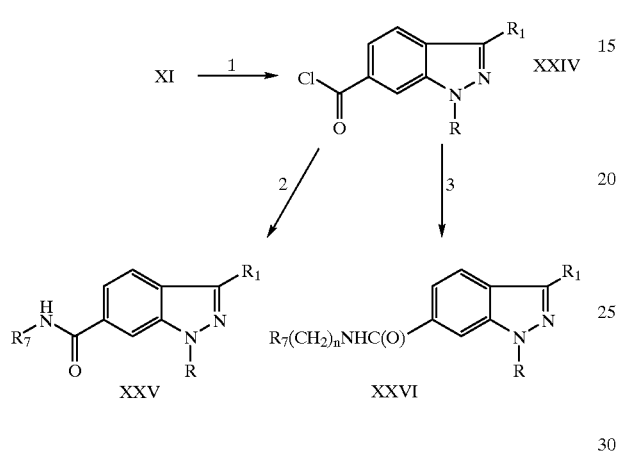
Scheme 5
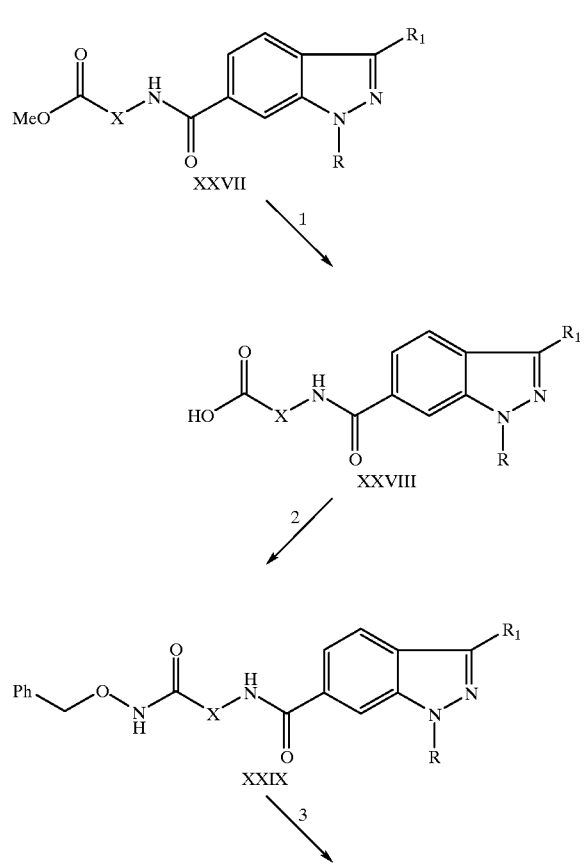
Scheme 6
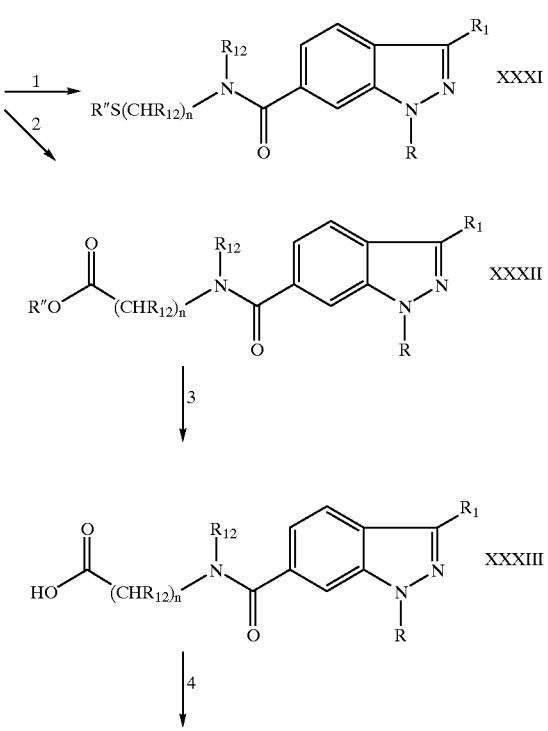
Scheme 7
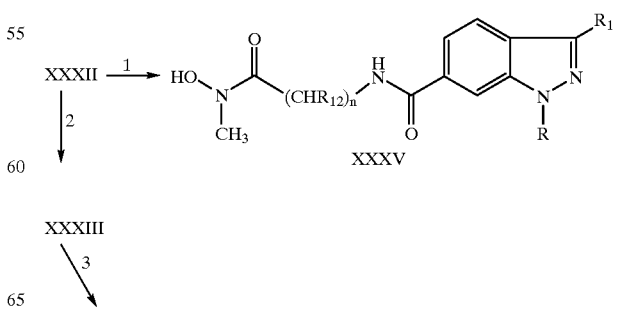

-continued

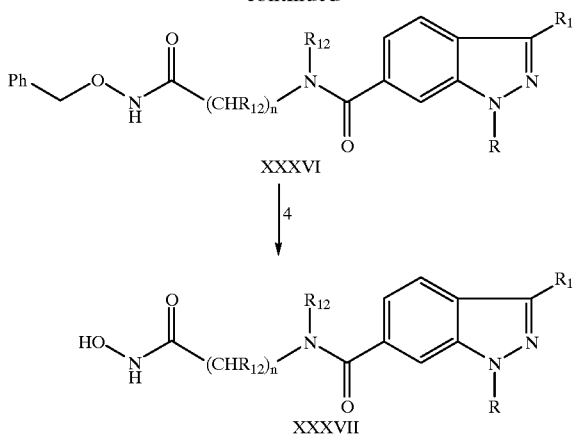

XXXVI

↓ 4

XXXVII

Scheme 8

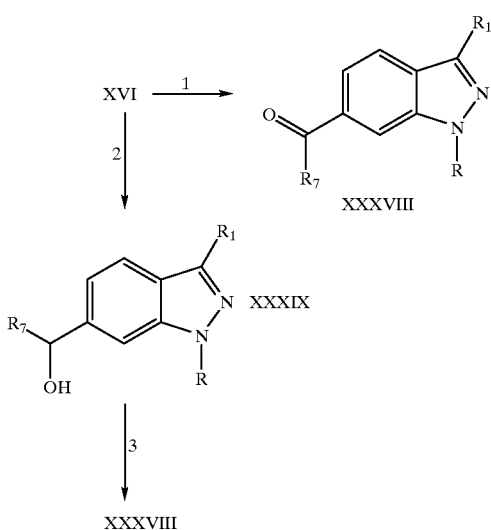

XXXVIII

The preparation of compounds of formula I can be carried out by one skilled in the art according to one or more of the synthetic methods outlined in Schemes 1–8 above and the examples referred to below. In step 1 of Scheme 1, the carboxylic acid of formula II, which is available from known commercial sources or can be prepared according to methods known to those skilled in the art, is nitrated under standard conditions of nitration ($HNO_3/H_2SO_4$, 0° C.) and the resulting nitro derivative of formula III is hydrogenated in step 2 of Scheme 1 using standard hydrogenation methods ($H_2$—Pd/C under pressure) at ambient temperature (20–25° C.) for several hours (2–10 hours) to provide the compound of formula IV. In step 3 of Scheme 1, the amino benzoic acid of formula IV is reacted with a base such as sodium carbonate under aqueous conditions and gently heated until mostly dissolved. The reaction mixture is chilled to a lower temperature (about 0° C.) and treated with sodium nitrate in water. After about 15 minutes, the reaction mixture is slowly transferred to an appropriate container holding crushed ice and a strong acid such as hydrochloric acid. The reaction mixture is stirred for 10–20 minutes and then added, at ambient temperature, to a solution of excess t-butyl thiol in an aprotic solvent such as ethanol. The reaction mixture is acidified to a pH of 4–5 through addition of an inorganic base, preferably saturated aqueous $Na_2CO_3$, and the reaction mixture is allowed to stir at ambient temperature for 1–3 hours. Addition of brine to the reaction mixture, followed by filtration, provides the sulfide of formula V.

In step 4 of Scheme 1, the sulfide of formula V is converted to the corresponding indazole carboxylic acid of formula VI by reacting the sulfide of formula V with a strong base, preferably potassium t-butoxide, in dimethyl sulfoxide (DMSO) at ambient temperature. After stirring for several hours (1–4 hours), the reaction mixture is acidified with a strong acid, such as hydrochloric or sulfuric acid, and then extracted using conventional methods. In step 5 of Scheme 1, the indazole carboxylic acid of formula VI is converted to the corresponding ester of formula VII by conventional methods known to those skilled in the art. In step 6 of Scheme 1, the compound of formula VIII is provided through alkylation of the ester of formula VII by subjecting the ester to conventional alkylation conditions (strong base/ various alkylating agents and, optionally, a copper catalyst such as $CuBr_2$) in a polar aprotic solvent, such as tetrahydrofuran (THF), N-methylpyrrolidinone or dimethylformamide (DMF), at ambient or higher temperature (25–200° C.) for about 6–24 hours, preferably about 12 hours. In step 7 of Scheme 1, the compound of formula VIII is converted to the corresponding alcohol of formula IX by following conventional methods known to those skilled in the art for reducing esters to alcohols. Preferably, the reduction is effected through use of a metal hydride reducing agent, such as lithium aluminum hydride, in a polar aprotic solvent at a low temperature (about 0° C.). In step 8 of Scheme 1, the alcohol of formula IX is oxidized to the corresponding aldehyde of formula X according to conventional methods known to those skilled in the art. For example, the oxidation can be effected through use of a catalytic amount of tetrapropylammonium perrutenate and excess N-methylmorpholine-N-oxide, as described in J. Chem. Soc., Chem. Commun., 1625 (1987), in an anhydrous solvent, preferably methylene chloride. In step 9 of Scheme 1, the ester of formula VIII is converted to the corresponding acid of formula XI by methods known to those skilled in the art, such as by treating the starting compound with sodium hydroxide in methanol and heating the mixture to reflux for several hours (2 or more hours). The acid of formula XI, like the aldehyde of formula X, is a useful intermediate for the preparation of various compounds of formula I.

Scheme 2 illustrates an alternative method of preparing the aldehyde of formula X and the acid of formula XI, as well as a method of preparing the compound of formula XVII. In step 1 of Scheme 2, the compound of formula XII is nitrated using conventional nitration conditions (nitric and sulfuric acid) to provide the compound of formula XIII. In step 2 of Scheme 2, the nitro derivative of formula XIII is reduced to the corresponding amine of formula XIV according to conventional methods known to those skilled in the art. Preferably, the compound of formula XIII is reduced to the amine of formula XIV using anhydrous stannous chloride in an anhydrous aprotic solvent such as ethanol. In step 3 of Scheme 2, the amine of formula XIV is converted to the corresponding indazole of formula XV by preparing the corresponding diazonium tetrafluoroborates as described in A. Roe, *Organic Reactions*, Vol. 5, Wiley, New York, 1949, pp. 198–206, followed by phase transfer catalyzed cyclization as described in R. A. Bartsch and I. W. Yang, J. Het. Chem. 21, 1063 (1984). In step 4 of Scheme 2, alkylation of the compound of formula XV is performed using standard methods known to those skilled in the art (i.e. strong base, polar aprotic solvent and an alkyl halide) to provide the N-alkylated compound of formula XVI. In step 5 of Scheme 2, the compound of formula XVI is subjected to metal halogen exchange employing an alkyl lithium, such as n-butyl lithium, in a polar aprotic solvent, such as THF, at low temperature (−50° C.–100° C. (−78° C. preferred)) followed by quenching with DMF at low temperature and warming to ambient temperature to provide the aldehyde intermediate of formula X, or the mixture containing the compound of formula XVI is quenched with $CO_2$, warmed to ambient temperature, and then quenched with an acid, such as hydrochloric acid, to provide the acid of formula XI. In step 6 of Scheme 2, the compound of formula XVI is converted to a compound of formula I wherein $R_2$ is $R_{19}$ which, as defined above, represents an aryl, heteroaryl, or heterocyclic moiety. In step 6 of Scheme 2, the compound of formula XVII is prepared by reacting the compound of formula XVI with a compound of formula $R_{19}$—$B(OH)_2$, wherein $R_{19}$ is as defined above, in the presence of $Pd(PPh_3)_4$ in aqueous $Na_2CO_3$ at reflux for about 4 hours.

Scheme 3 illustrates the preparation of a compound of formula I wherein $R_1$ is H and $R_2$ is —C(O)NHR$_7$ wherein $R_7$ is as defined above. In step 1 of Scheme 3, the compound of formula XVIII is treated with boron trifluoride etherate in ethanol-free chloroform at a temperature of about −20° C. After a short period, such as about 5 minutes, t-butyl nitrite is added to the mixture and the reaction is stirred at about 0° C. for about 2 hours. Potassium acetate followed by 18-crown-6 are then added to provide the compound of formula XIX (1H-indazole-6-carboxylic acid). In step 2 of Scheme 3, the compound of formula XIX is treated with concentrated sulfuric acid in methanol at reflux for about 8 hours followed by stirring at ambient temperature for about 18 hours to provide the compound of formula XX. In step 3 of Scheme 3, the compound of formula XX is reacted with a compound of the formula R—X, wherein R is as defined above and X is a leaving group such as chloro, bromo, or iodo, preferably bromo, in the presence of sodium hydride in DMF for about 10–24 hours, preferably 24 hours, at ambient temperature to provide the ester of formula XXI. In step 4 of Scheme 3, the ester of formula XXI is converted to the acid of formula XXII in accord with the procedure of step 9 of scheme 1. In step 5 of Scheme 3, the compound of formula XXII is treated with thionyl chloride and DMF (as a catalyst) in anhydrous toluene at reflux for about 3 hours to provide the corresponding acid chloride. Separately, a compound of the formula $R_7$—$NH_2$, wherein $R_7$ is as defined above, is added to a mixture of sodium hydride in anhydrous THF which is cooled to a temperature of about 0° C. To this second mixture, the acid chloride, referred to above, in THF is added and the mixture is stirred at ambient temperature for a period of 4–24 hours to provide the compound of formula XXIII.

Scheme 4 illustrates the preparation of compounds of formula I wherein $R_2$ is —C(O)NHR$_7$ or —C(O)NH(CH$_2$)$_n$R$_7$, wherein n is 1 to 4, and $R_7$ is as defined above. In step 1 of Scheme 4, the acid of formula XI is converted to the corresponding acid chloride of formula XXIV by treating the starting compound with thionyl chloride and DMF (as a catalyst) in anhydrous toluene at reflux for about 3 hours. The acid chloride of formula XXIV can be converted to the compound of formula XXV by reacting the starting compound with a compound of the formula $R_7$—$NH_2$, wherein $R_7$ is as defined above, in the presence of sodium hydride in anhydrous THF at a temperature of about 0° C., followed by warming to ambient temperature, for a period of 4–24 hours. This method is preferred where $R_7$ is substituted or unsubstituted pyridinyl. In the alternative, the compound of formula XXIV can be converted to the compound of formula XXV by reacting the starting compound with a compound of the formula $R_7$—$NH_2$, wherein $R_7$ is as defined above, in the presence of sodium hydride in anhydrous DMF at ambient temperature for a period of 4–24 hours. This method is preferred where $R_7$ is substituted or unsubstituted pyrimidinyl. In the alternative, the compound of formula XXIV can be converted to the compound of formula XXV by adding a compound of the formula $R_7$—$NH_2$, wherein $R_7$ is as defined above, to the reaction mixture in which the acid chloride is prepared and then heating the mixture to a temperature of about 200° C. for a short period, such as about 15 minutes.

In step 3 of Scheme 4, the compound of formula XXIV is converted to the compound of formula XXVI, wherein n is 1 to 4 and $R_7$ is as defined above, by reacting the starting compound with a compound with a compound of the formula $H_2N$—C(O)NH(CH$_2$)$_n$R$_7$, wherein n is 1 to 4, and $R_7$ is as defined above, in the presence of triethylamine, and optionally dimethylaminopyridine (DMAP), in methylene chloride at ambient temperature for about 10–48 hours. In the alternative, the compound of formula XXIV can be converted to the compound of formula XXVI by reacting the starting compound with a compound of the formula $H_2N$—(CH$_2$)$_n$R$_7$, wherein n is 1 to 4, and $R_7$ is as defined above, in anhydrous pyridine at about 40° C. for about 1 hour. This alternative method for step 3 of Scheme 4 is preferred where $R_7$ is a nitrogen-containing heterocyclic moiety such as pyridinyl.

Scheme 5 illustrates the preparation of compounds of formula I wherein $R_2$ is —$Z_3$—$R_7$ wherein $Z_3$ is —C(O)NH— and $R_7$ is aryl, such as phenyl or naphthyl, substituted by —C(O)NHOH. Scheme 5 begins with a compound of the formula XXVII, wherein X is an aryl moiety, as the starting material. The compound of formula XXVII is prepared according to the method illustrated in Scheme 4. In step 1 of Scheme 5, the compound of formula XXVII is hydrolyzed to the corresponding acid of formula XXVIII which can be done according to methods known to those skilled in the art, such as by treating the compound of formula XXVII with sodium hydroxide in methanol at reflux for about 30 minutes to 1 hour. In step 2 of Scheme 5, the acid of formula XXVIII is converted to the compound of formula XXIX by treating the acid with 1-(3-dimethylaminopropyl)-3-ethylcarbodiimide hydrochloride and O-benzylhydroxylamine hydrochloride in methylene chloride at ambient temperature for about 4–24 hours. In step 3 of Scheme 5, the compound of formula XXIX is converted to the compound of formula XXX by treating the starting compound with 10% Pd/C in ethyl acetate and methanol under an $H_2$ atmosphere (about 30 psi) at ambient temperature for about 30 minutes to 1 hour.

Scheme 6 illustrates the preparation of compounds of formula I wherein $R_2$ is —C(O)NR$_{12}$(CHR$_{12}$)$_m$SR$^m$ (compound of formula XXXI), wherein R$^m$ is $C_1$–$C_4$ alkyl, m is 1 to 6, and $R_{12}$ is as defined above, or wherein $R_2$ is —C(O)NR$_{12}$(CHR$_{12}$)$_m$C(O)NHOMe (compound of formula XXXIV), wherein $R_{12}$ is as defined above, m is 1 to 6, and Me is methyl. In step 1 of Scheme 6, the compound of formula XI is treated with a compound of the formula $H_2N$—(CHR$_{12}$)$_m$SR$^m$, wherein R$^m$, $R_{12}$ and m are as defined above, 1-(3-dimethylaminopropyl)-3-ethylcarbodiimide hydrochloride, and triethylamine in methylene chloride at ambient temperature for a period of about 18 hours to provide the compound of formula XXXI. In step 2 of Scheme 6, the compound of formula XXXII is prepared in accord with the method illustrated in Scheme 4. In step 3 of Scheme 6, the compound of formula XXXIII is prepared by heating to reflux the compound of formula XXXII in ethanol or methanol and sodium hydroxide for about 1 hour. In step 4 of Scheme 6, the compound of formula XXXIV is prepared by treating the compound of formula XXXIII with methoxylamine hydrochloride, 1-(3-dimethylaminopropyl)-3-ethylcarbodiimide hydrochloride, 1-hydroxybenzotriazole hydrate and triethylamine in methylene chloride at ambient temperature for a period of about 18 hours.

Scheme 7 illustrates the preparation of compounds of formula I wherein $R_2$ is —C(O)NH(CHR$_{12}$)$_m$C(O)N(CH$_3$)OH (compound of formula XXXV), wherein m is 1 to 6, or wherein $R_2$ is —C(O)NR$_{12}$(CHR$_{12}$)$_m$C(O)NHOH (compound of formula XXXVII), wherein $R_{12}$ is as defined above and m is 1 to 6. In step 1 of Scheme 7, the compound of formula XXXV is prepared by treating the compound of formula XXXII with sodium and N-methylhydroxylamine hydrochloride in methanol at ambient temperature for about 16 hours. In step 2 of Scheme 7, the compound of formula XXXIII is prepared in accord with step 3 of Scheme 6. In step 3 of Scheme 7, the compound of formula XXXVI is prepared by treating the compound of formula XXXIII with O-benzylhydroxylamine, 1-hydroxybenzotriazole hydrate, 1-(3-dimethylaminopropyl)-3-ethylcarbodiimide hydrochloride, and triethylamine in methylene chloride at ambient temperature for a period of about 18 hours. In step 4 of Scheme 7, the compound of formula XXXVII is prepared by treating the compound of formula XXXVI with 10% Pd/C in methanol and ethyl acetate under a $H_2$ atmosphere (about 30 psi) at ambient temperature for about 30 minutes to 1 hour.

Scheme 8 illustrates the preparation of compounds of formula XXXVIII. In step 1 of Scheme 8, the compound of formula XVI, which is prepared according to the method of Scheme 2, is treated with n-butyl lithium in anhydrous THF at a low temperature, such as about −78° C., for about 30 minutes, followed by quenching the mixture with a compound of the formula $R_7$—CN, wherein $R_7$ is as defined above, and allowing the mixture to warm to ambient temperature over a period of about 30 minutes to 1 hour to provide the compound of formula XXXVIII. This method of preparing the compound of formula XXXVIII is preferred for compounds in which $R_7$ is a nitrogen-containing heteroaryl moiety. Steps 2 and 3 of Scheme 8 illustrate an alternative method of preparing the compound of formula XXXVIII which is preferred for those compounds in which $R_7$ is a substituted or unsubstituted aryl moiety. In step 2 of Scheme 8, the compound of formula XVI is treated as described in step 1 of Scheme 8 except a compound of the formula $R_7$—C(O)H is substituted for the compound of formula $R_7$—CN, wherein $R_7$ is as defined above. In step 3 of Scheme 8, the compound of formula XXXIX is oxidized to provide the compound of formula XXXVIII according to methods known to those skilled in the art as described in step 8 of Scheme 1.

The compounds of formula I can also be prepared following one or more synthetic methods that are disclosed in issued patents or published patent applications. In particular, using the intermediates described in Schemes 1–8, referred to above, in particular the intermediates of formulas VIII, X, XI, XVI, and XXIV, those skilled in the art can prepare the compounds of formula I using analogous synthetic methods that have been described for compounds in which a phenyl ring is substituted for the indazole ring in the compounds of formula I. Such analogous synthetic methods are disclosed in the following issued patents and published patent applications: U.S. Pat. No. 5,449,676 (issued Sep. 12, 1995); U.S. Pat. No. 5,459,151 (issued Oct. 17, 1995); U.S. Pat. No. 5,491,147 (issued Feb. 13, 1996); European patent application EP 470,805 (published Feb. 12, 1992); European patent application EP 497,564 (published Aug. 5, 1992); European patent application EP 723,962 (published Jul. 15, 1996); WO 92/00968 (published Jan. 23, 1992); WO 93/15044 (published Aug. 5, 1993); WO 93/15045 (published Aug. 5, 1993); WO 93/18024 (published Sep. 16, 1993); WO 93/25517 (published Dec. 23, 1993); WO 94/02465 (published Feb. 3, 1994); WO 95/01338 (published Jan. 12, 1995); WO 95/04045 (published Feb. 9, 1995); WO 95/04046 (published Feb. 9, 1995); WO 95/05386 (published Feb. 23, 1995); WO 95/20578 (published Aug. 3, 1995); WO 95/22520 (published Aug. 24, 1995); WO 95/27692 (published Oct. 19, 1995); WO 96/00218 (published Jan. 4, 1996); and WO 96/21435 (published Jul. 18, 1996). The foregoing issued patents and published European and PCT international patent applications are incorporated herein by reference in their entirety.

Specifically, the compounds of formula I wherein $R_2$ is —$Z_3$—$R_7$ can be prepared by following analogous synthetic methods disclosed in WO 94/02465, WO 95/01338, WO 93/25517, WO 95/20578, WO 96/00218 and EP 497,564, each of which is referred to above. The compounds of formula I wherein $R_2$ is $R_{19}$ can be prepared by following analogous synthetic methods disclosed in U.S. Pat. No. 5,491,147, WO 95/27692 and WO 95/22520, each of which is referred to above. The compounds of formula I wherein $R_2$ is a substituent of formula (If) or (Ig) can be prepared by following analogous synthetic methods disclosed in WO 95/22520, which is referred to above. The compounds of formula I wherein $R_2$ is a substituent of formula (Ih) can be prepared by following analogous synthetic methods disclosed in U.S. Pat. No. 5,459,151, which is referred to above. The compounds of formula I wherein $R_2$ is —C(=NOC(O)$R_{25}$)$R_{26}$ can be prepared by following analogous synthetic methods disclosed in EP 470,805, which is referred to above. The compounds of formula I wherein $R_2$ is —(CR$_{17}$R$_{18}$)$_m$NR$_9$(C(O))$_q$R$_{10}$ can be prepared by following analogous synthetic methods disclosed in WO 92/00968, WO 95/05386, WO 93/15044, and WO 93/15045, each of which is referred to above. The compounds of formula I wherein $R_2$ is —CR$_{17}$R$_{18}$CHR$_{28}$NR$_9$SO$_2$(CH$_2$)$_p$A, —CR$_{17}$R$_{18}$CHR$_{28}$NR$_9$P(O)(OR$_{12}$)C(O)(C$_1$–C$_4$ alkyl), or —CR$_{17}$R$_{18}$CHR$_{28}$NR$_9$P(O)(C$_1$–C$_4$ alkoxy)$_2$ can be prepared by following analogous synthetic methods disclosed in WO 95/05386, which is referred to above. The compounds of formula I wherein $R_2$ is a substituent of formula (Ic), (Id) or (Ie) can be prepared by following analogous synthetic methods disclosed in WO 93/18024, which is referred to above. The compounds of formula I wherein $R_2$ is a substituent of formula (Ii) can be prepared by following analogous synthetic methods disclosed in EP 723,962, which is referred to above. The compounds of formula I wherein $R_2$ is —C(=NR$_{32}$)NH(CH$_2$)$_p$(C$_8$–C$_{10}$ aryl) can be prepared by following analogous synthetic methods disclosed in WO 96/21435, which is referred to above.

The compounds of formula I can be resolved into separate enantiomers by using a chiral LC technique according to the following conditions: column: Chiralcel® OD (250×4.6 mm); mobile phase: 50:50:0.1 (Hexane:2-propanol:diethylamine); flow rate: 1 mL/minute; detection: UV (230 nm); temperature: ambient (20–25° C.); injection volume: 20 µL. The compounds of formula I can also be resolved into separate enantiomers according to other techniques familiar to those skilled in the art, including those described in J. March, *Advanced Organic Chemistry*, (4th Edition, J. Wiley & Sons), 1992, pages 118–125.

The compounds of formula I that are basic in nature are capable of forming a wide variety of different salts with various inorganic and organic acids. Although such salts must be pharmaceutically acceptable for administration to animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Cationic salts of the compounds of formula I are similarly prepared except through reaction of a carboxy group with an appropriate cationic salt reagent such as sodium, potassium, calcium, magnesium, ammonium, N,N'-dibenzylethylenediamine, N-methylglucamine (meglumine), ethanolamine, tromethamine, or diethanolamine.

For administration to humans in the curative or prophylactic treatment of inflammatory diseases, a variety of conventional routes may be used including orally, parenterally, topically, and rectally (suppositories), in single or divided doses. Oral dosages of a compound of formula I or a pharmaceutically acceptable salt thereof (the "active compounds") are generally in the range of 0.1 to 1000 mg daily for an average adult patient (70 kg), in single or divided doses. Individual tablets or capsules should generally contain from 0.1 to 100 mg of active compound, in a suitable pharmaceutically acceptable vehicle or carrier. Dosages for intravenous administration are typically within the range of 0.1 to 10 mg per single dose as required. For intranasal or inhaler administration, the dosage is generally formulated as a 0.1 to 1% (w/v) solution. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and all such dosages are within the scope of this invention.

For administration to humans for the inhibition of TNF, a variety of conventional routes may be used including orally, parenterally, topically, and rectally (suppositories), in single or divided doses. In general, the active compound will be administered orally or parenterally at dosages between about 0.1 and 25 mg/kg body weight of the subject to be treated per day, preferably from about 0.3 to 5 mg/kg, in single or divided doses. However, some variation in dosage will necessarily occur depending on the condition of the subject being treated. The person responsible for administration will, in any event, determine the appropriate dose for the individual subject.

For human use, the active compounds of the present invention can be administered alone, but will generally be administered in an admixture with a pharmaceutical diluent or carrier selected with regard to the intended route of administration and standard pharmaceutical practice. For example, the active compounds can be administered orally in the form of tablets containing such excipients as starch or lactose, or in capsules either alone or in admixture with excipients, or in the form of elixirs or suspensions containing flavoring or coloring agents. The active compounds may be injected parenterally; for example, intravenously, intramuscularly or subcutaneously. For parenteral administration, the active compounds are best used in the form of a sterile aqueous solution which may contain other substance; for example, enough salts or glucose to make the solution isotonic.

Additionally, the active compounds may be administered topically when treating inflammatory conditions of the skn and this may be done by way of creams, jellies, gels, pastes, and ointments, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The ability of the compounds of formula I or the pharmaceutically acceptable salts thereof to inhibit PDE IV may be determined by the following assay.

Thirty to forty grams of human lung tissue is placed in 50 ml of pH 7.4 Tris/phenylmethylsulfonyl fluoride (PMSF)/sucrose buffer and homogenized using a Tekmar Tissumizer® (Tekmar Co., 7143 Kemper Road, Cincinnati, Ohio 45249) at full speed for 30 seconds. The homogenate is centrifuged at 48,000 xg for 70 minutes at 4° C. The supernatant is filtered twice through a 0.22 $\mu$m filter and applied to a Mono-Q FPLC column (Pharmacia LKB Bioltechnology, 800 Centennial Avenue, Piscataway, N.J. 08854) pre-equillibrated with pH 7.4 Tris/PMSF Buffer. A flow rate of 1 ml/minute is used to apply the sample to the column, followed by a 2 ml/minute flow rate for subsequent washing and elution. Sample is eluted using an increasing, step-wise NaCl gradient in the pH 7.4 Tris/PMSF buffer. Eight ml fractions are collected. Fractions are assayed for specific $PDE_{IV}$ activity determined by [$^3$H]cAMP hydrolysis and the ability of a known $PDE_{IV}$ Inhibitor (e.g. rolipram) to inhibit that hydrolysis. Appropriate fractions are pooled, diluted with ethylene glycol (2 ml ethylene glycol/5 ml of enzyme prep) and stored at −20° C. until use.

Compounds are dissolved in dimethylsulfoxide (DMSO) at a concentration of 10 mM and diluted 1:25 in water (400 $\mu$M compound, 4% DMSO). Further serial dilutions are made in 4% DMSO to achieve desired concentrations. The final DMSO concentration is the assay tube is 1%. In duplicate the following are added, in order, to a 12×75 mm glass tube (all concentrations are given as the final concentrations in the assay tube).

i) 25 $\mu$l compound or DMSO (1%, for control and blank)
ii) 25 $\mu$l pH 7.5 Tris buffer
iii) [$^3$H]cAMP (1 $\mu$M)
iv) 25 $\mu$l PDE IV enzyme (for blank, enzyme is preincubated in boiling water for 5 minutes)

The reaction tubes are shaken and placed in a water bath (37° C.) for 20 minutes, at which time the reaction is stopped by placing the tubes in a boiling water bath for 4 minutes. Washing buffer (0.5 ml, 0.1M 4-(2-hydroxyethyl)-1-piperazine-ethanesulfonic acid (HEPES)/0.1M naci, pH 8.5) is added to each tube on an ice bath. The contents of each tube are filed to an AFF-Gel 601 column (Biorad Laboratories, P.O. Box 1229, 85A Marcus Drive, Melville, N.Y. 11747)(boronate affinity gel, 1 ml bed volume) previously equillibrated with washing buffer. [$^3$H]cAMP is washed with 2×6 ml washing buffer, and [$^3$H]5'AMP is then eluted with 4 ml of 0.25M acetic acid. After vortexing, 1 ml of the elution is added to 3 ml scintillation fluid in a suitable vial, vortexed and counted for [$^3$H].

% inhibition=1−average cpm (test compound−average cmp (blank)/average cpm (control—average cpm (blank)

$IC_{80}$ is defined as that concentration of compound which inhibits 50% of specific hydrolysis of [$^3$H]cAMP to [$^3$H]5'AMP.

The ability of the compounds I or the pharmaceutically acceptable salts thereof to inhibit the production of TNF and, consequently, demonstrate their effectiveness for treating disease involving the production of TNF is shown by the following in vitro assay:

Peripheral blood (100 mls) from human volunteers is collected in ethylenediaminetetraacetic acid (EDTA). Mononuclear cells are isolated by FICOLL/Hypaque and washed three times in incomplete HBSS. Cells are resuspended in a final concentration of 1×10$^6$ cells per ml in pre-warmed RPMI (containing 5% FCS, glutamine, pen/step and nystatin). Monocytes are plated as 1×10$^4$ cells in 1.0 ml in 24-well plates. The cells are incubated at 37° C. (5% carbon dioxide) and allowed to adhere to the plates for 2 hours, after which time non-adherent cells are removed by gentle washing. Test compounds (10 μl) are then added to the cells at 3–4 concentrations each and incubated for 1 hour. LPS (10 μl) is added to appropriate wells. Plates are incubated overnight (18 hrs) at 37° C. At the end of the incubation period TNF was analyzed by a sandwich ELISA (R&D Quantikine kit). $IC_{50}$ determinations are made for each compound based on linear regression analysis.

The following Examples illustrate the invention. In the following Examples, "min." means minute(s), "psi" means pounds per square inch, "h" means hour(s), "equiv" means equivalent(s), and "conc." means concentrated.

PREPARATION 1

1-Cyclopentyl-3-Ethyl-1H-Indazole-6-Carboxylic Acid Methyl Ester

A. 3-Nitro-4-propyl-benzoic acid.

9.44 g (57.5 mmol, 1.0 equiv) of 4-propylbenzoic acid were partially dissolved in 50 mL concentrated $H_2SO_4$ and chilled in an ice bath. A solution of 4.7 mL (74.7 mmol, 1.3 equiv) concentrated $HNO_3$ in 10 ml concentrated $H_2SO_4$ was added dropwise over 1–2 min. After stirring 1 hour at 0° C., the reaction mixture was poured into a 1 L beaker half full with ice. After stirring 10 min., the white solid that formed was filtered, washed 1×$H_2O$, and dried to give 12.01 g (100%) of the title compound: mp 106–109° C.; IR (KBr) 3200–3400, 2966, 2875, 2667, 2554, 1706, 1618, 1537, 1299, 921 cm$^{-1}$; $^1$H NMR (300 MHz, DMSO-d$_8$) δ0.90 (t, 3H J=7.4 Hz), 1.59 (m, 2H), 2.82 (m, 2H), 7.63 (d, 1H, J=8.0 Hz), 8.12 (dd, 1H, J=1.7, 8.0 Hz), 8.33 (d, 1H, J=1.7 Hz); $^{13}$C NMR (75.5 MHz, DMSO-d$_8$) δ14.2, 23.7, 34.2, 125.4, 130.5, 132.9, 133.6, 141.4, 149.5, 165.9; Anal. calcd for $C_{10}H_{11}NO_4$·¼$H_2O$: C, 56.20; H, 5.42; N, 6.55. Found: C, 56.12; H, 5.31;N, 6.81.

B. 3-Amino-4-propyl-benzoic acid.

A mixture of 11.96 g (57.2 mmol) 3-nitro-4-propyl-benzoic acid and 1.5 g 10% Pd/C, 50% water wet, in 250 ml. $CH_3OH$ was placed on a Parr hydrogenation apparatus and shaken under 25 psi $H_2$ at ambient temperature (20–25° C). After 1 hour, the reaction mixture was filtered through Celite®(trademark)SiO$_2$ based filtering agent), and the filtrate concentrated and dried to give 9.80 g (96%) of a pale yellow crystalline solid: mp 139.5–142.5° C.; IR (KBr) 3200–2400, 3369, 3298, 2969, 2874, 2588, 1690, 1426, 1260, 916, 864 cm$^{-1}$; $^1$H NMR (300 MHz, DMSO-d$_6$) δ0.90 (t, 3H, J=7.2 Hz), 1.52 (m, 2H), 2.42 (m,2H), 5.08 (br s, 2H), 6.96 (d, 1H, J=7.8 Hz), 7.05 (dd, 1H, J=1.7, 7.8 Hz), 7.20 (d, 1H, J=1.7 Hz), MS (Cl, $NH_3$) m/z 180 (M+H$^+$, base); anal. calcd for $C_{10}H_{13}NO_2$·⅓$H_2O$: C, 64.85; N, 7.89; N, 7.56. Found: C, 64.69; H, 7.49; N, 7.86.

C. 3-Carboxy-6-propyl-benzenediazo t-butyl sulfide.

A mixture of 8.80 g (49.1 mmol, 1.0 equiv) 3-amino-4-propyl-benzoic acid and 2.34 g (22.1 mmol, 0.45 equiv) sodium carbonate in 55 mL $H_2O$ was heated gently with a heat gun until mostly dissolved. The reaction mixture was chilled in an ice bath, and a solution of 3.73 g (54.0 mmol, 1.0 equiv) sodium nitrite in 27 mL $H_2O$ was added dropwise. After 15 minutes, the reaction mixture was transferred to a dropping funnel and added over 10 minutes to a beaker containing 55 g of crushed ice and 10.6 mL concentrated HCl. After stirring 10 minutes, the contents of the beaker were transferred to a dropping funnel and added over 5 minutes to a room temperature solution of 5.31 mL (47.1 mmol, 0.96 equiv) t-butyl thiol in 130 mL ethanol. The pH was adjusted to 4–5 by addition of saturated aqueous $Na_2CO_3$ solution, and the reaction mixture was allowed to stir 1 hour at ambient temperature (20–25° C.). 200 mL brine were added, and the mixture was filtered. The solid was washed 1×$H_2O$ and dried overnight to give 12.25 g (89%) of a brown/rust colored powder (caution-stench): mp 102° C. (dec); IR (KBr) 3200–2400, 2962, 2872, 2550, 1678, 1484, 1428, 1298, 1171 cm$^{-1}$; $^1$H NMR (300 MHz, DMSO-d$_6$) δ0.84 (t, 3H, J=7.3 Hz), 1.48 (m, 2H), 1.55 (s, 9H), 2.42 (m, 2H), 7.29 (d, 1H, J=1.6 Hz), 7.50 (d, 1H, J=8.0 Hz), 7.86 (dd, 1H, j=1.7, 7.9 Hz), 13.18 (br s, 1H); MS (thermospray, $NH_4OAc$) m/z 281 (M+H+, base); Anal. calcd for $C_{14}H_{20}N_2O_2S$: C, 59.96; H, 7.19; N, 9.99. Found: C, 59.71; H, 7.32; N, 10.02.

D. 3-Ethyl-1H-indazole-6-carboxylic acid.

A solution of 12.0 g (42.8 mmol, 1.0 equiv) 3-carboxy-6-propyl-benzenediazo t-butyl sulfide in 150 mL dimethyl-sulfoxide (DMSO) was added dropwise over 15 minutes to an ambient temperature solution of 44.6 g (398 mmol, 9.3 equiv) potassium tert-butoxide in 200 mL DMSO. After stirring 2hours at ambient temperature, the reaction mixture was poured into 1.5 L of 0° C 1N HCl, stirred 5 minutes, then extracted 2×350 mL ethyl acetate. The ethyl acetate extracts (caution-stench) were combined, washed 2×250 mL $H_2O$, and dried over $MgSO_4$. Filtration, concentration of filtrate and drying gave a tan solid, which was triturated with 1L of 1:3 $Et_2O$/Hexanes and dried to give 7.08 g (87%) of a tan crystalline powder: mp 248–251° C.; IR(KBr)3301, 3300–2400,2973, 2504, 1702, 1455, 1401, 1219 cm$_{-1}$; $^1$H NMR (300 MHz, DMSO-d$_6$) δ1.31 (t,3H, j×7.6 Hz), 2.94 (q,2H, J=7.6 Hz), 7.63 (dd, 1H, J=1.1,8.4 Hz), 7.81 (d, 1H, J=8.4 Hz), 8.06 (d, 1H, J=1.1. Hz), 12.95 (br s, 1H); MS (Cl, $NH_3$) m/z 191 (M+H+, base); Anal. calcd for $C_{10}H_{10}N_2O_2$:C, 63.14; H, 5.30; N, 14.73. Found: C,62.66; H, 5.42; N, 14.80.

E. 3-Ethyl-2H-indazole-6-carboxylic acid methyl ester.

8.78 g (45.8 mmol, 1.1 equiv) 1-(3-dimethylaminopropyl)-3-ethylcarbodiimide hydrochloride were added in one portion to an ambient temperature solution of 7.92 g (41.6 mmol, 1.0 equiv) 3- ethyl-1H-indazole-6-carboxylic acid, 16.9 mL (416 mmol, 10 equiv) methanol and 5.59 g (45.8 mmol, 1.1 equiv) dimethylaminopyridine (DMAP) in 250 mL $CH_2Cl_2$. After 18 hours at room temperature, the reaction mixture was concentrated to 150 mL, diluted with 500 mL ethyl acetate, washed 2×100 mL 1N HCl, 1×100 mL $H_2O$, 1×100 mL brine, and dried over $Na_2SO_4$. Filtration, concentration of filtrate and drying gave 7.8 g of a brown solid, which was purified on a silica gel column (30% to 50% ethyl acetate/hexane gradient) to give 6.41 g (75%) of a tan solid: mp 107–108° C.; IR (KBr) 3100–2950, 1723, 1222 $cm^{-1}$; $^1$H NMR (300 MHz, $CDCl_3$) δ8.19 (m, 1H), 7.7–7.8 (m, 2H), 3.96 (s, 3H), 3.05 (q, 2H, J=7.7 Hz), 1.43 (t, 3H, 7.7 Hz); MS (Cl, $NH_3$) m/z 205 (M+H$^+$, base); Anal. calcd for $C_{11}H_{12}N_2O_2$: C, 64.70; H, 5.92; N, 13.72. Found: C, 64.88; H, 6.01; N, 13.96.

F. 1-Cyclopentyl-3-ethyl-1H-indazole-6-carboxylic acid methyl ester.

1.17 g (29.4 mmol, 1.05 equiv) sodium hydride, 60% oil dispersion, were added in one portion to an ambient temperature solution of 5.7 g (27.9 mmol, 1.0 equiv) 3-ethyl-1H- indazole-6-carboxylic acid methyl ester in 125 mL anhydrous DMF. After 20 min., 3.89 mL (36.6 mmol, 1.3 equiv) cyclopentyl bromide were added dropwise, and the reaction mixture allowed to stir overnight at room temperature. The mixture was then poured into 1 L $H_2O$ and extracted 3+450 mL ethyl acetate. The organic extracts were combined, washed 3×400 mL $h_2O$, 1×200 mL brine, and dried over $Na_2SO_4$. Filtration, concentration of filtrate and drying gave an amber oil, which was purified on a silica gel column (10% ethyl acetate/hexanes, gravity) to give 5.48 g (72%) of a clear oil: $^1$H NMR (300 MHz, $CDCl_3$)δ8.16 (d, 1H, J=1.0 Hz), 7.7 (m, 2H), 500 quintet, 1H, J=7.5Hz), 3.97 (s, 3H), 3.01 (q, 2H, J=7.6 Hz), 2.2 (m, 4H), 2.0 (m, 2H), 1.8 (m, 2H). 1.39 (t, 3H, J=7.6 Hz); HRMS calcd for $C_{18}H_{20}N_2O_2$: 272.15026. Found: 272.15078.

G. (1-Cyclopentyl-3-ethyl-1H-indazol-6-yl)-methanol.

7 ml (7.0 mmol, 1.0 equiv) lithium aluminum hydride, 1.0M solution in tetrahydrofuran (THF), were added to a 0° C. solution of 1.02 g (7.05 mmol, 1.0 equiv) 1-cyclopentyl-3-ethyl-1H-indazole-6-carboxylic acid methyl ester in 50 mL anhydrous THF. After 20 minutes, 1 mL methanol was added cautiously, then the reaction mixture was poured into 500 mL of 5% $H_2SO_4$ and extracted 3×50 mL ethyl acetate. The organic extracts were combined, washed 2×40 mL $H_2O$, 1×40 mL brine, and dried over $Na_2SO_4$. Filtration, concentration of filtrate, and drying gave 1.58 g of a clear oil, which was purified on a silica gel column to give 1.53 g (89%) clear oil: IR ($CHCl_3$) 3606, 3411, 3009, 2972, 2875, 1621, 1490 $cm^{-1}$, $^1$H NMR (300 Mhz, $CDCl_3$) δ7.65 (d, 1H, J=8.0 Hz) 7.42 (s, 1H), 7.06 (dd, 1H, J=1.0, 8.2 Hz), 4.92 (quintet, 1H, J=7.7 Hz), 4.84 (s, 2H), 2.98 (q, 2H, J=7.6 Hz), 2.2 (m, 4H), 2.0 (m, 2H), 1.7 (m, 3H), 1.38 (t, 3H, J=7.6 Hz); MS (thermospray, $NH_4OAc$) m/z 245 (M+H$^+$. base); HRMS calcd for $C_{15}H_{20}N_2$ O+H: 245.1654. Found: 245.1675.

H. 1-Cyclopentyl-3-ethyl-1H-indazole-6-carbaldehyde.

106 mg (0.301 mmol, 0.05 equiv) tetrapropylammonium perruthenate (VII) were added to a room temperature suspension of 1.47 g (6.02 mmol, 1.0 equiv) (1-cyclopentyl-3-ethyl-1H-indazol-6-yl)-methanol, 1.06 g (9.03 mmol, 1.5 equiv) N-methylmorpholine N-oxide and 3.01 g 4A molecular sieves in 12 mL anhydrous $CH_2Cl_2$. After 20 minutes the reaction mixture was filtered through a short column of silica gel (eluted with $CH_2Cl_2$). Fractions containing product were concentrated, and the residue chromatographed on a silica gel column (15% ethyl acetate/hexanes, flash) to give 924 mg (63% of a pale yellow solid: mp 41° C.; IR (KBr) 3053, 2966, 2872, 2819, 1695 $cm^{-1}$; $^1$H NMR (300 MHz, $CDCl_3$) δ10.13 (s, 1H), 7.93 (d, 1H, J-0.9 Hz), 7.77 (d, 1H, J=8.4 Hz), 7.60 (dd, 1H, J=1.2, 8.4 Hz), 5.00 (quintet, 1H, J=7.5 Hz), 3.01 (q, 2H, J-7.6 Hz), 2.2 (m, 4H), 2.2 (m, 2H), 1.7 (m, 2H), 1.39 (t, 3H, J=7.5 Hz); MS (Cl, $NH_3$) m/z 243 (M+H$^+$, base); Anal. calcd for $C_{16}H_{18}N_2O$: C, 74.35; H, 7.49; N, 11.58. Found: C, 74.17; H, 7.58; N, 11.79.

PREPARATION 2

1-Cyclopentyl-3-Ethyl-1H-Indazole-6-Carbaldehyde

A. 4-Bromo-2-nitro-1-propyl-benzene.

125 g (628 mmol, 1.0 equiv) 1-bromo-4-propyl-benzene were added in one portion to a 10° C. solution of 600 mL conc. $H_2SO_4$ and 200 mL $H_2O$. With vigorous mechanical stirring, an ambient temperature mixture of 43.2 mL (691 mmol, 1.1 equiv) conc. $HNO_3$ (69–71%, 16M) in 150 mL conc. $H_2SO_4$ and 50 mL $H_2O$ was added dropwise over 30 minutes. The ice bath was allowed to warm to ambient temperature, and the reaction stirred at room temperature for 68 hours. The reaction mixture was poured into a 4 L beaker, loosely packed full with crushed ice. After stirring 1 hour, the mixture was transferred to a 4 L separatory funnel and extracted 4×800 mL isopropyl ether. The organic extracts were combined, washed 3×800 mL $H_2O$, 1×500 mL brine, and dried over $Na_2SO_4$. Filtration, concentration of filtrate and drying gave 150 mL of a yellow liquid, which was purified by silica gel chromatography (2columns, 3 kg silica gel each, 2% ethyl acetate/hexanes) to afford 63.9 g (42%) of a yellow liquid. The less polar regioisomer is the less polar of the two, which are formed in a 1:1 ratio. bp 108° C., 2.0 mm; IR ($CHCl_3$) 3031, 2966, 2935, 2875, 1531, 1352 $cm^{-1}$H NMR (300 MHz, $CDCl_3$)δ8.01 (d, 1H, J=2.1 Hz), 7.62 (dd, 1H, J=2.1, 8.3 Hz) 7.23 (d, 1H, J=8.3 Hz), 2.81 (m, 2H), 1.67 (m, 2H), 0.98 (t, 3H, J=7.4 Hz); $^{13}$C NMR (75.5 MHz, $CDCl_3$) δ13.94, 23.74, 34.43, 119.6, 127.4, 133.3, 135.7, 136.4, 149.8; GCMS (El) m/z 245/243 (M+.), 147 (base); HRMS calcd for $C_9H_{10}NO_2Br+H$: 243.9973. Found: 243.9954.

B. 5-Bromo-2-propyl-phenylamine.

121 g (639 mmol, 3.0 equiv) of stannous chloride (anhydrous) were added in one portion to a room temperature solution of 51.9 g (213 mmol, 1.0 equiv) 4-bromo-2-nitro-2-propyl-benzene in 1200 mL absolute ethanol and 12 mL (6equiv) $H_2O$. After 24 hours at room temperature, most of the ethanol was removed on a rotary evaporator. The residue was poured into a 4 L beaker, ¾ full with crushed ice and $H_2O$. 150 g of NaOH pellets were added portionwise, with stirring, until the PH=10 and most of the tin hydroxide was dissolved. The mixture was divided in half, and each half extracted 1×750 mL ethyl acetate. All four ethyl acetate extracts were combined, washed 2×500 mL each 1N NaOH, $H_2O$, and brine, then dried over $Na_2SO_4$. Filtration, concentration of filtrate and drying gave a yellow liquid, which was purified on a 1.2 kg silica gel column (1:12 ethyl acetate/hexanes) to give 41.83 g (95%) of a pale yellow liquid: IR ($CHCl_3$) 3490, 3404, 3008, 2962, 2933, 2873, 1620, 1491 $cm^{-1}$; $^1$H NMR (300 MHz, $CDCl_3$) δ6.8–6.9 (m, 3H), 3.90 (br s, 2H), 2.42 (m,2H), 1.62 (m, 2H), 0.99 (t, 3H, J=7.3 Hz); GCMS (El) m/z 215/213 (M+.), 186/184 (base); Anal. calcd for $C_9H_{12}NBr$: C, 50.49; H, 5.65; N, 6.54. Found: C, 50.77; H, 5.70; N, 6.50.

C. 6-Bromo-3-ethyl-1H-indazole.

49.22 g (230 mmol, 1.0 equiv) 5-bromo-2-propylphenylamine were placed in a 3 L flask and chilled in an ice bath. A 0° C. solution of 57.5 mL (690 mmol, 3.0 equiv) conc. HCl in 165 mL H$_2$O was added, and the resulting solid mass which formed was ground up until a fine white suspension resulted. 100 mL more H$_2$O were added, then a solution of 15.9 g (230 mmol, 1.0 equiv) sodium nitrite in 75 mL H$_2$O were added dropwise over 10 minutes. The ice bath was removed, and the reaction allowed to stir at room temperature for 30 minutes. The reaction mixture was then filtered through a sintered glass funnel, precooled to 0° C. The filtrate was chilled in an ice bath, and with mechanical stirring, a 0° C. solution/suspension of 32.8 g (313 mmol, 1.36 equiv) ammonium tetrafluorobrate in 110 mL H$_2$O was added dropwise over 10 minutes. The thick white suspension which formed (aryl diazonium tetrafluoroborate salt) was allowed to stir 1.5 hours at 0° C. The mixture was then filtered, and the solid washed 1×200 mL 5% aq. NH$_4$BF$_4$ (cooled at 0° C.), 1×150 mL CH$_3$OH (cooled to 0° C.), then 1×200 mL Et$_2$O. Drying at high vacuum, ambient temperature for 1 hour gave 54.47 g (76%) of the diazonium salt, an off-white solid.

1500 mL of ethanol free chloroform were placed in a 3-neck flask, then 34.16 g (348 mmol, 2.0 equiv) potassium acetate (powdered and dried) and 2.3 g (8.7 mmol, 0.05 equiv) 18-crown-6 were added. After 10 minutes, the diazonium salt was added in one portion, and the reaction mixture allowed to stir at room temperature under nitrogen atmosphere for 18 hours. The mixture was then filtered, the solid washed 2 × with CHCl$_3$, and the filtrate concentrated to give 47 g of crude product (brown crystals). Silica gel chromatography (1.2 kg silica gel, ethyl acetate/hexanes gradient 15%, 20%, 40%) gave 21.6 g (55% for second step, 42% overall) of tan crystals: mp 112–114° C.; IR (KBr) 3205, 3008, 2969, 2925, 1616, 1340, 1037 cm$^{-1}$, $^1$H NMR (300 MHz, CDCl$_3$) δ9.86 (br s, 1H), 7.61 (d, 1H, J=1.3 Hz), 7.57 (d, 1H, J=8.4 Hz), 7.24 (dd, 1H, J=1.5, 8.6 Hz), 2.99 (q, 2H, J=7.6 Hz), 1.41 (t, 3H, J=7.6 Hz); MS (Cl, NH$_3$) m/z 227/225 (M+H$^{30}$, base); Anal. calcd for C$_8$H$_8$N$_2$Br: C, 48.02; H, 4.03; N, 12.45. Found: C, 48.08; H, 3.87; N, 12.45.

D. 6-Bromo-1-cyclopentyl-3-ethyl-1H-indazole. 2.46 g (61.04 mmol, 1.05 equiv) sodium hydride, 60% oil dispersion, were added in 0.5 g portion to a 10° C. solution of 13.17 g (58.5 mmol, 1.0 equiv) 6-bromo-3-ethyl-1H-indazole in 500 mL anhydrous DMF. The mixture was stirred at ambient temperature for 20 minutes, then a solution of 8.8 mL (81.92 mmol, 1.4 equiv) cyclopentyl bromide in 10 mL anhydrous DMF was added dropwise. After 18 hours, the reaction mixture was poured into 2 L H$_2$O and extracted 2×1 L ethyl acetate. The organic extracts were combined, washed 2×750 ml H$_2$O, 1×500 mL brine, and dried over Na$_2$SO$_4$. Filtration, concentration of filtrate and drying gave 20.7 g of crude product, which was purified on a silica gel column (1.1 kg silica gel, 3% ethyl acetate/hexanes) to give 10.6 g (62%) of an amber liquid: IR (CHCl$_3$) 2972, 2875, 1606, 1501, 1048 cm$^{-1}$; $^1$H NMR (300 mHz, CDCl$_3$)δ7.56 (d, 1H, J=1.3 Hz), 7.52 (d, 1H, J=8.7 Hz), 7.17 (dd, 1H, J×1.5, 8.5 Hz), 4.83 (quintet, 1H, J=7.6 Hz), 2.96 (q, 2H, J=7.6 Hz), 2.15 (m, 4H), 2.0 (m, 2H), 1.65 (m, 2H), 1.36 (t, 3H, J=7.7 Hz); MS (thermospray, NH$_4$OAc) m/z 295/293 (M+H+, base); Anal. calcd for C$_{14}$H$_{17}$N$_2$Br: C, 57.35 ; H, 5.84; N, 9.55 . Found: C, 57.48; H, 5.83; N, 9.90.

E. 1-Cyclopentyl-3-ethyl-2H-indazole-6-carbaldehyde.

11.6 mL (28.4 mmol, 1.0 equiv) n-BuLi, 2.45M in hexanes, were added to a −78° C. solution of 8.32 g (28.4 mmol, 1.0 equiv) 6-bromo-1-cyclopentyl-3-ethyl-1H-indazole in 200 mL anhydrous THF. After 30 min. at −78° C., 8.8 mL (114 mmol, 4.0 equiv) anhydrous DMF were added dropwise, and the reaction mixture was allowed to stir an additional 30 minutes at −78° C. The mixture was warmed to room temperature over 1hour, then 125 mL 1N HCl were added. After stirring for 10 minutes, most of the THF was removed on a rotary evaporator. The residue was diluted with 500 mL H$_2$O, and extracted 2×250 mL ethyl acetate. The organic extracts were combined, washed 1×100 mL H$_2$O, 1×100 mL brine, and dried over Na$_2$SO$_4$. Filtration, concentration of filtrate and drying gave a yellow oil, which was purified on silica gel column (15% ethyl acetate/hexanes, gravity) to give 4.70 g (68%) of a yellow crystalline solid: $^1$H NMR (300 MHz, CDCl$_3$) identical to the spectrum of the title compound from Preparation 1.

PREPARATION 3

1-Cyclopentyl-3-Ethyl-1H-Indazole-6-Carboxylic Acid

A. 3-Nitro-4-propylbenzoic acid 9.44 g (57.5 mmol, 1.0 equiv) of 4-propyl-benzoic acid were partially dissolved in 50 mL conc. H$_2$SO$_4$ and chilled in an ice bath. A solution of 4.7 mL (74.7 mmol, 1.3 equiv) conc. HNO$_3$ in mL conc. H$_2$SO$_4$ was added dropwise over 1–2 minutes. After stirring 1 hour at 0° C., the reaction mixture was poured into a 1 L beaker half full with ice. After stirring 10 minutes, the white solid which formed was filtered, washed 1×H$_2$O, and dried to give 12.01 g (100%) of the title compound: mp 106–109° C.; IR (KBr) 3200–3400, 2966, 2875, 2667, 2554, 1706, 1618, 1537, 1299, 921 cm$^{-1}$; $^1$H NMR (300 MHz, DMSO-d$_6$) δ0.90 (t, 3H, J=7.4 Hz), 1.59 (m, 2H), 2.82 (m, 2H), 7.63 (d, 1H, J=8.0 Hz), 8.12 (dd, 1H, J=1.7, 8.0 Hz), 8.33 (d, 1H, J=1.7 Hz); $^{13}$C NMR (75.5 MHz, DMSO-d$_6$) δ14.2, 23.7, 34.2, 125.4, 130.5, 132.9, 133.6, 141.4, 149.5, 165.9; Anal. calcd for C$_{10}$H$_{11}$NO$_4$·¼H$_2$O: C, 56.20; H, 5.42; N, 6.55. Found: C, 56.12; H, 5.31; N, 6.81.

B. 3-Amino-4-propyl-benzoic acid

A mixture of 11.96 g (57.2 mmol) 3-nitro-4-propyl-benzoic acid and 1.5 g 10% pd/C, 50 % water wet, in 250 mL CH$_3$OH was placed on a Parr hydrogenation apparatus and shaken under 25 psi H$_2$ at ambient temperature. After 1h, the reaction mixture was filtered through Celite®, and the filtrate concentrated and dried to give 9.80 g (96%) of a pale yellow crystalline solid: mp 139.5–142.5° C.; IR(KBr) 3200–2406, 3369, 3298, 2969, 2874, 2588, 1690, 1426, 1260, 916, 864 cm$^{-1}$, $^1$H NMR (300 MHz, DMSO-d$_6$) δ0.90 (t, 3H, J=7.2 Hz), 1.52 (m, 2H), 2.42 (m, 2H), 5.08 (br s, 2H), 6.96 (d, 1H, J=7.8 Hz), 7.05 (dd, 1H, J–1.7, 7.8 Hz), 7.20 (d, 1H, J=1.7 Hz); MS (CI, NH$_3$)m/z 180 M+H$^{30}$ , base); Anal. calcd for C$_{10}$H$_{13}$NO$_2$. ⅓H$_2$O: C, 64.85; N, 7.89; N, 7.56. Found: C, 64.69; H, 7.49; N, 7.86.

C. 3-Carboxy-6-propyl-benzenediazo t-butyl sulfide

A mixture of 8.80 g (49.1 mmol, 1.0 equiv) 3-amino-4-propyl-benzoic acid and 2.34 g (22.1 mmol, 0.45 equiv) sodium carbonate in 55 mL H$_2$O was heated gently with a heat gun until most dissolved. The reaction mixture was chilled in an ice bath, and a solution of 3.73 g (54.0 mmol, 1.0 equiv) sodium nitrite in 27 mL H$_2$O was added dropwise. After 15 minutes, the reaction mixture was transferred to a dropping funnel and added over 10 minutes to a beaker containing 55 g of crushed ice and 10.6 mL conc. HCl. After stirring 10 minutes, the contents of the beaker were transferred to a dropping funnel and added over 5 minutes to a room temperature solution of 5.31 mL (47.1 mmol, 0.96 equiv) t-butyl thiol in 130 mL ethanol. The pH was adjusted to 4–5 by addition of saturated aqueous $Na_2CO_3$ solution, and the reaction mixture was allowed to stir 1 hour at ambient temperature. 200 mL brine were added, and the mixture was filtered. The solid was washed 1×$H_2O$ and dried overnight to give 12.25 g (89%) of a brown/rust colored powder (caution-stench): mp 102° C. (dec); IR (KBr) 3200–2400, 2962, 2872, 2550, 1678, 1484, 1428, 1298, 1171 $cm^{-1}$; $^1H$ NMR (300 MHz, DMSO-$d_6$) δ 0.84 (t, 3H, J=7.3 Hz), 1.48 (m, 2H), 1.55 (s, 9H), 2.42 (m, 2H), 7.29 (d, 1H, J=1.6 Hz), 7.50 (d, 1H, J=8.0 Hz), 7.86 (dd, 1H, J=1.7, 7.9 Hz), 13.18 (br s, 1H); MS (thermospray, $NH_4OAc$) m/z 281 (M+H+, base); Anal. calcd for $C_{14}H_{20}N_2O_2S$: C, 59.96; H, 7.19; N, 9.99. Found: C, 59.71; H, 7.32; N, 10.02.

D. 3-Ethyl-1H-indazole-6-carboxylic acid

A solution of 12.0 g (42.8 mmol, 1.0 equiv) 3-carboxy-6-propyl-benzenediazo t-butyl sulfide in 150 mL DMSO was added dropwise over 15 minutes to a room temperature solution of 44.6 g (398 mmol, 9.3 equiv) potassium t-butoxide in 200 mL DMSO. After stirring 2 hours at ambient temperature, the reaction mixture was poured into 1.5 L of 0° C. 1N HCl, stirred 5 minutes, then extracted 2×350 mL ethyl acetate. The ethyl acetate extracts (caution-stench) were combined, washed 2×250 mL $H_2O$, and dried over $MgSO_4$. Filtration, concentration of filtrate and drying gave a tan solid, which was triturated with 1 L of 1:3 $Et_2O$/Hexanes and dried to give 7.08 g (87%) of a tan crystalline powder: mp 248–251° C.; IR (KBr) 3301, 3300–2400, 2973, 2504, 1702, 1455, 1401, 1219 $cm^{-1}$; $^1H$ NMR (300 MHz, DMSO-$d_6$) δ 1.31 (t, 3H, J=7.6 Hz), 2.94 (q, 2H, J=7.6 Hz), 7.63 (dd, 1H, J=1.1, 8.4 Hz), 7.81 (d, 1H, J=8.4 Hz), 8.06 (d, 1H, J=1.1 Hz), 12.95 (br s, 1H); MS (Cl, $NH_3$) m/z 191 (M+H+, base); Anal. calcd for $C_{10}H_{10}N_2O_2$: C, 63.14; H, 5.30; N, 14.73. Found: C, 62.66; H, 5.42; N, 14.80.

E. 3-Ethyl-1H-indazole-6-carboxylic acid methyl ester 8.78 g (45.6 mmol, 1.1 equiv) 1-(3-dimethylaminopropyl)-3-ethylcarbodiimide hydrochloride were added in one portion to a room temperature solution of 7.92 g (41.6 mmol, 1.0 equiv) 3-ethyl-1H-indazole-6-carboxylic acid, 16.9 mL (416 mmol, 10 equiv) methanol and 5.59 g (45.8 mmol, 1.1 equiv) DMAP in 250 mL $CH_2Cl_2$. After 18 hours at room temperature, the reaction mixture was concentrated to ~150 mL, diluted with 500 mL ethyl acetate, washed 2×100 mL 1N HCl, 1×100 mL $H_2O$, 1×100 mL brine, and dried over $Na_2SO_4$. Filtration, concentration of filtrate and drying gave 7.8 g of a brown solid, which was purified on a silica gel column (30% to 50% ethyl acetate/hexanes gradient) to give 6.41 g (75%) of a tan solid: mp 107–108° C.; IR (KBr) 3100–2950, 1723, 1222 $cm^{-1}$; $^1H$ NMR (300 MHz, $CDCl_3$) δ 8.91 (m, 1H), 7.7–7.8 (m, 2H), 3.96 (s, 3H), 3.05 (q, 2H, J=7.7 Hz), 1.43 (t, 3H, 7.7 Hz); MS (Cl, $NH_3$) m/z 205 (M+H+, base); Anal. calcd for $C_{11}H_{12}N_2O_2$: C, 64.70; H, 5.92; N, 13.72. Found: C, 64.88; H, 6.01; N, 13.96.

F. 1-Cyclopentyl-3-ethyl-1H-indazole-6-carboxylic acid methyl ester 1.17 g (29.4 mmol, 1.05 equiv) sodium hydride, 60% oil dispersion, were added in one portion to a room temperature solution of 5.7 g (27.9 mmol, 1.0 equiv) 3-ethyl-1H-indazole-6-carboxylic acid methyl ester in 125 mL anhydrous DMF. After 20 minutes, 3.89 mL (36.6 mmol, 1.3 equiv) cyclopentyl bromide were added dropwise, and the reaction mixture allowed to stir overnight at room temperature. The mixture was then poured into 1 L $H_2O$ and extracted 3×400 mL $H_2O$, 1×200 mL brine, and dried over $Na_2SO_4$. Filtration, concentration of filtrate and drying gave an amber oil, which was purified on a silica gel column (10% ethyl acetate/hexanes, gravity) to give 5.48 g (72%) of a clear oil: $^1H$ MR (300 MHz, $CDCl_3$) δ 8.16 (d, 1H, J=1.0 Hz), 7.7 (m, 2H), 500 (quintet, 1H, J=7.5 Hz), 3.97 (s, 3H), 3.01 (q, 2H, J=7.6 Hz), 2.2 (m, 4H), 2.0 (m, 2H), 1.8 (m, 2H), 1.39 (t, 3H, J=7.6 Hz); HRMS calc for $C_{16}H_{20}N_2O_2$: 272.1526. Found: 272.15078.

G. 1-Cyclopentyl-3-ethyl-1H-indazole-6-carboxylic acid

A mixture of 5.24 g (19.2 mmol, 1.0 equiv) 1-cyclopentyl-3-ethyl-1H-indazole-6-carboxylic acid methyl ester in 120 mL methanol and 60 mL 1N NaOH was heated to reflux. After 1 hours, the reaction mixture was cooled to room temperature, concentrated to 75 mL, acidified to pH=1 with 1N HCl, and extracted 2×200 mL ethyl acetate. The organic extracts were combined, washed 1×150 mL $H_2O$, 1×150 mL brine, and dried over $Na_2SO_4$. Filtration, concentration of filtrate and drying gave 4.79 g (96%) of a white solid. A small sample was recrystallized from ethyl acetate/hexanes to obtain analytical data: mp 157–159° C.; IR (KBr) 3100–2500, 1683, 1298 $cm^{-1}$; $^1H$ NMR (300 MHz, DMSO-$d_6$) δ 13.0 (br s, 1H), 8.21 (s, 1H), 7.79 (d, 1H, J=7.9 Hz), 7.62 (sdd, 1H, J=1.2, 8.4 Hz), 5.18 (quintet, 1H, J=7.5 Hz), 2.92 (q, 2H, J=7.6 Hz), 2.1 (m, 2H), 2.0 (m, 2H), 1.85 (m, 2H), 1.6 (m, 2H), 1.29 (t, 3H, J=7.6 Hz); MS (Cl, $NH_3$) m/z 259 (M+H+, base); Anal. calcd for $C_{15}H_{18}N_2O_2$: C, 69.74; H, 7.02; N, 10.85. Found: C, 69.77; H, 7.02; N, 10.85.

EXAMPLE 1

2-Cyclopentyl-2H-indazole-6-carboxylic acid(3,5-dichloro-pyridin-4-yl)amide and 1-Cyclopentyl-2H-indazole-6-carboxylic acid (3,5-dichloro-pyridin-4-yl)amide 1.A 1H-Indazole-6-carboxylic acid A partial solution of 15.1 g (100 mmol, 1.0 equiv) 3-amino-4-methylbenzoic acid in 150 mL anhydrous THF was added dropwise at a −20° C. solution of 18 mL (146 mmol, 1.46 equiv) boron trifluoride etherate in 450 mL ethanol free chloroform. After 5 minutes, 14 mL (106 mmol, 1.06 equiv) of 90% t-butyl nitrite were added dropwise, and the reaction stirred at 0° C. for 2 hours. 49 g (500 mmol, 5.0 equiv) potassium acetate were added portion wise, followed by 2.65 g (10 mmol, 0.1 equiv) 18-crown-6 in one portion. The reaction mixture was allowed to stir at room temperature for 48 hours, then was concentrated on a rotary evaporator. 500 mL of 3:7 acetone/ethyl acetate and 150 mL 1N HCl were added, and the mixture stirred for 2 hours. 150 mL brine were added and the mixture was filtered. The filtrate was transferred to a separatory funnel, the layers separated, and the aqueous layer extracted 2×100 mL 3:7 acetone/ethyl acetate. The organic layers were combined and dried over $MgSO_4$. Filtration and concentration of the filtrate gave a solid, to which were added 250 mL of acetic acid. The suspension was heated on a steam bath until mostly dissolved, then was removed from the steam bath and 300 mL of ethereal HCl (prepared by passing HCl (g) through 350 mL $Et_2O$, chilled in an ice bath, for 10 minutes) were added slowly to the still hot acetic acid solution. 250 mL $Et_2O$ were added and the mixture stirred at room temperature for 1 hour. Filtration and drying gave a golden brown powder. The powder was suspended in 500 mL of 3:7 acetone/ethyl acetate, 100 mL brine were added, and the mixture stirred for 1 hour at room temperature. The layers were separated, and the aqueous layer was extracted 1×100 mL ethyl acetate. The combined organic layers were dried over $MgSO_4$. Filtration, concentration of filtrate and drying at high vacuum, room temperature for 18 hours gave 7.81 g (48%) of a brown powder: mp >275° C.; MS (Cl, $NH_3$) m/z 180 (M+18+, base).

1.B 1H-Indazole-6-carboxylic acid methyl ester

A mixture of 7.59 g (46.8 mmol, 1.0 equiv) 1H-indazole-6-carboxylic acid in 500 mL $CH_3OH$ and 1 mL conc. $H_2SO_4$ was heated to reflux for 8 hours, then allowed to stir at room temperature for 18 hours. The mixture was concentrated to ~200 mL, diluted with 1 L ethyl acetate, and washed 1×250 mL saturated aqueous $NaHCO_3$, 1×250 mL $H_2O$, 1×250 mL brine, and dried over $Na_2SO_4$. The aqueous washes were extracted with two portions of ethyl acetate to recover additional product. The organic layers were combined, concentrated, and dried to give 6.75 g (82%) of a yellow-orange-tan solid: $^1$H NMR (300 MHz, $CDCl_3$) δ 10.8 (br s, 1H), 8.28 (dd, 1H, J=0.9, 1.9 Hz), 8.15 (d, 1H, J=1.0 Hz), 7.8 (m, 2H), 3.97 (s, 3H): MS (Cl, $NH_3$) m/z 177 (M+H$^+$, base).

1.C 1-Cyclopentyl-1H-indazole-6-carboxylic acid methyl ester and 2-cyclopentyl-2H-indazole-6-carboxylic acid methyl ester 1.60 g (39.9 mmol, 1.05 equiv) sodium hydride, 60% oil dispersion, were added in one portion to a room temperature solution of 6.70 g (38.0 mmol, 1.0 equiv) 1H-indazole-6-carboxylic acid methyl ester in 150 mL anhydrous DMF. After 30 minutes, 4.5 mL (41.8 mmol, 1.1 equiv) cyclopentyl bromide were added dropwise, and the mixture stirred at room temperature for 24 hours. The reaction mixture was diluted with 1.2 liters of ethyl acetate, washed 3×350 mL $H_2O$, 1×250 mL brine, and dried over $Na_2SO_4$. Filtration, concentration of filtrate and drying gave 12 g of an amber oil, which was purified on a 700 g silica gel column (20% ethyl acetate/hexanes, flash) to give 4.26 g of 1-cyclopentyl-1H-indazole-6-carboxylic acid methyl ester (46% yield, less polar isomer) and 3.66 g of 2-cyclopentyl-2H-indazole-6-carboxylic acid methyl ester (39% yield, more polar isomer). Both compounds were orange oils: data for 1H-indazole regioisomer: IR ($CHCl_3$) 2996, 2955, 2874, 1717, 1249 cm$^{-1}$; HRMS calcd for $C_{14}H_{18}N_2O_2$:244.1213; found: 244.1209; data for 2H-indazole regioisomer: IR ($CHCl_3$) 2972, 2955, 2876, 1714, 1242 cm$^{-1}$; HRMS calcd for $C_{14}H_{18}N_2O_2$: 244.1213. Found: 244.1220.

1.D 1-Cyclopentyl-1H-indazole-6-carboxylic acid

A mixture of 3.93 g (16.1 mmol, 1.0 equiv) of 1-cyclopentyl-1H-indazole-6-carboxylic acid methyl ester, 100 mL $CH_3OH$ and 50 mL 1N NaOH was heated to reflux for 30 minutes. The reaction mixture was cooled to room temperature, and most of the $CH_3OH$ removed on a rotary evaporator. The residue was diluted with 325 mL $H_2O$ and acidified to pH=1 with 2N HCl. After stirring 5 minutes, the mixture was filtered, and the solid washed 2×$H_2O$ and dried overnight to give 3.42 g (92%) of a yellow powder: mp 172–175° C.; Anal. calcd for $C_{13}H_{14}N_2O_2$: C, 67.79; H, 6.13; N, 12.16. Found: C, 67.62; H 5.82; N, 12.19.

1.E 2-Cyclopentyl-2H-indazole-6-carboxylic acid

This compound was prepared according to the method of Example 1.D, starting with 3.28 g (13.4 mmol) 2-cyclopentyl-2H-indazole-6-carboxylic acid methyl ester, 100 mL $CH_3OH$ and 40 mL 1N NaOH, to give 2.71 g (88%) of light yellow powder: mp 190–193° C.; Anal. calcd for $C_{13}H_{14}N_2O_2$: C, 67.79; H, 6.13; N, 12.16. Found: C, 67.40; H, 6.04; N, 12.38.

1.F 1-Cyclopentyl-1H-indazole-6-carboxylic acid (3,5-dichloro-pyridin-4-yl) amide A suspension of 495 mg (2.15 mmol, 1.0 equiv) 1-cyclopentyl-1H-indazole-6-carboxylic acid, 204 μL (2.79 mmol, 1.3 equiv) thionyl chloride, and 10 μL DMF in 10 mL anhydrous toluene was heated to reflux for 3 hours, then cooled to ambient temperature and concentrated to dryness on a rotary evaporator. In a separate flask, a solution of 333 mg (2.04 mmol, 0.95 equiv) 3,5-dichloro-4-aminopyridine in 10 mL anhydrous THF was added dropwise to a 0° C. suspension of 198 mg (4.95 mmol, 2.3 equiv) sodium hydride, 60% oil dispersion, in 10 mL anhydrous THF. The mixture was stirred for 15 minutes at room temperature, then was recooled to 0° C. A solution of the acid chloride (prepared above) in 10 mL anhydrous THF was added dropwise, and the reaction mixture allowed to stir at room temperature overnight. 4.5 mL 1N HCl were added dropwise to the reaction mixture, which was then diluted with 200 mL $CH_2Cl_2$, washed 1×30 mL each $H_2O$, 10% aqueous $Na_2CO_3$, $H_2O$, then dried over $Na_2SO_4$. Purification on a silica gel column (2% $CH_3OH/CH_2Cl_2$, flash) gave 0.76 g (94%) of product, a yellow amorphous foam: $^1$H NMR (300 MHz, $CDCl_3$) δ 8.58 (s, 2H), 8.19 (d, 1H, J=0.9 Hz), 8.09 (d, 1H, J=0.7 Hz), 7.93 (br s, 1H), 7.84 (dd, 1H, J=0.7, 8.4 Hz), 7.63 (dd, 1H, J=1.4, 8.4 Hz), 5.08 (quintet, 1H), 2.2 (m, 4H), 2.0 (m, 2H), 1.75 (m, 2H); MS (Cl, $NH_3$) m/z 375 (M+H$^+$, base); Anal. calcd for $C_{18}H_{18}N_4OCl_2$: C, 57.62; H, 4.30; N, 14.93; found: C, 57.68; H, 4.55; N, 14.55.

1.G 2-Cyclopentyl-2H-indazole-6-carboxylic acid (3,5-dichloro-pyridin-4-yl)amide This compound was prepared according to the method of Example 1.F, using 424 mg of 2-cyclopentyl-2H-indazole-6-carboxylic acid as starting material to give 406 mg (59%) of a white amorphous foam: $^1$H NMR (300 MHz, $CDCl_3$) δ 8.57 (s, 2H), 8.36 (d, 1H, J=1.4 Hz), 8.06 (d, 1H, J=0.7 Hz), 7.84 (br s, 1H), 7.78 (dd, 1H, J=0.7, 8.6 Hz), 7.64 (dd, 1H, J=8.7 Hz), 5.00 (quintet, 1H), 2.35 (m, 2H), 2.25 (m, 2H), 2.0 (m, 2H), 1.8 (m, 2H); MS (Cl, $NH_3$), m/z 375 (M+H$^+$, base); Anal. calcd for $C_{18}H_{16}N_4OCl_2$: C, 57.621 H, 4.30; N, 14.93. Found: C, 57.39; H, 4.59; N, 14.56.

EXAMPLE 2

3-Nitro-4-propyl-benzoic acid 9.44 g (57.5 mmol, 1.0 equiv) of 4-propylbenzoic acid were partially dissolved in 50 mL conc. $H_2SO_4$ and chilled in an ice bath. A solution of 4.7 mL (74.7 mmol, 1.3 equiv) conc. $HNO_3$ in 10 mL conc. $H_2SO_4$ was added dropwise over 1–2 min. After stirring 1 h at 0° C., the reaction mixture was poured into a 1 L beaker half full with ice. After stirring 10 min., the white solid which formed was filtered, washed 1×$H_2O$, and dried to give 12.01 g (100%) of the title compound: mp 106–109° C.: IR (KBr) 3200–3400, 2966, 2875, 2667, 2554, 1706, 1618, 1537, 1299, 921 cm$^{-1}$; $^1$H NMR (300 MHz, DMSO-$d_6$) δ 0.90 (t, 3H, J=7.4 Hz), 1.59 (m, 2H), 2.82 (m, 2H), 7.63 (d, 1H, J=8.0 Hz), 8.12 (dd, 1H, J=1.7, 8.0 Hz), 8.33 (d, 1H, J=1.7 Hz); $^{13}$C NMR (75.5 MHz, DMSO-$D_6$) δ 14.2, 23.7, 34.2, 125.4, 130.5, 132.9, 133.6, 141.4, 149.5, 165.9; Anal. calcd for $C_{10}H_{11}NO_4 \cdot \frac{1}{4}H_2O$: C, 56.20; H, 5.42; N, 6.55. Found: C, 56.12; H, 5.31; N, 6.81.

EXAMPLE 3

3-Amino-4-propyl-benzoic acid

A mixture of 1.96 g (57.2 mmol) 3-nitro-4-propyl-benzoic acid and 1.5 g 10% Pd/C, 50% water wet, in 250 mL $CH_3OH$ was placed on a Parr hydrogenation apparatus and shaken under 25 psi $H_2$ at ambient temperature. After 1 h, the reaction mixture was filtered through Celite®, and the filtrate concentrated and dried to give 9.80 g (96%) of a pale yellow cyrstalline solid: mp 139.5–142.5° C.; IR (KBr) 3200–2400, 3369, 3298, 2969, 2874, 25588, 1690, 1426, 1260, 916, 864 cm$^{-1}$; $^1$H NMR (300 MHz, DMSO-$D_6$) δ 0.90 (t, 3H, J=7.2 Hz), 1.52 (m, 2H), 2.42 (m, 2H), 5.08 (br s, 2H), 6.96 (d, 1H, J=7.8 Hz), 7.05 (dd, 1H, J=1.7, 7.8 Hz), 7.20 (d, 1H, J=1.7 Hz); MS (Cl, $NH_3$) m/z 180 (M+H$^+$, base); Anal. calcd for $C_{10}H_{13}NO_2 \cdot \frac{1}{3}H_2O$; C, 64.85; N, 7.89; N, 7.56. Found: C, 64.69; H, 7.49; N, 7.86.

EXAMPLE 4

3-Carboxy-6-propyl-benzenediazo t-butyl sulfide

A mixture of 8.80 g (49.1 mmol, 1.0 equiv) 3-amino-4-propyl-benzoic acid and 2.34 g (22.1 mmol, 0.45 equiv) sodium carbonate in 55 mL $H_2O$ was heated gently with a heat gun until mostly dissolved. The reaction mixture was chilled in an ice bath, and a solution of 3.73 g (54.0 mmol, 1.0 equiv) sodium nitrite in 27 mL $H_2O$ was added dropwise. After 15 min., the reaction mixture was transferred to a dropping funnel and added over 10 min. to a beaker containing 55 g of crushed ice and 10.6 mL conc. HCl. After stirring 10 min., the contents of the beaker were transferred to a dropping funnel and added over 5 min. to a room temperature solution of 5.31 mL (47.1 mmol, 0.96 equiv) t-butyl thiol in 130 mL ethanol. The pH was adjusted to 4–5 by addition of saturated aqueous $Na_2CO_3$ solution, and the reaction mixture was allowed to stir 1 h at ambient temperature. 200 mL brine were added, and the mixture was filtered. The solid was washed 1×$H_2O$ and dried overnight to give 12.5 g (89%) of a brown/rust colored powder (caution-stench): mp 102° C. (dec); IR (KBr) 3200–2400, 2962, 2872, 2550, 1678, 1484, 1428, 1298, 1171 cm$^{-1}$; $^1$H NMR (300 MHz, DMSO-$d_6$) δ 0.84 (t, 3H, J=7.3 Hz), 1.48 (m, 2H), 1.55 (s, 9H), 2.42 (m, 2H), 7.29 (d, 1H, J=1.6 Hz), 7.50 (d, 1H, J=8.0 Hz), 7.86 (dd, 1H, J=1.7, 7.9 Hz), 13.18 (br s, 1H); MS (thermospray, $NH_4OAc$) m/z 281 (M+H+, base); Anal. calcd for $C_{14}H_{20}N_2O_2S$: C, 59.96; H, 7.19; N, 9.99. Found: C, 59.71; H, 7.32; N, 10.02.

EXAMPLE 5

3-Ethyl-1H-indazole-6-carboxylic acid

A solution of 12.0 g (42.8 mmol, 1.0 equiv) 3-carboxy-6-propyl-benzenediazo t-butyl sulfide in 150 mL DMSO was added dropwise over 15 min. to a room temperature solution of 44.6 g (398 mmol, 9.3 equiv) potassium t-butoxide in 200 mL DMSO. After stirring 2 h at ambient temperature, the reaction mixture was poured into 1.5 L of 0° C. 1N HCl, stirred 5min., then extracted 2×350 mL ethyl acetate. The ethyl acetate extracts (caution-stench) were combined, washed 2×250 mL $H_2O$, and dried over $MgSO_4$. Filtration, concentration of filtrate and drying gave a tan solid, which was triturated with 1 L of 1:3 $Et_2O$/Hexanes and dried to give 7.08 g (87%) of a tan crystalline powder. mp 248–251° C.; IR (KBr) 3301, 3300–2400, 2973, 2504, 1702, 1455, 1401, 1219 cm$^{-1}$; $^1$H NMR (300 MHz, DMSO-$d_6$), δ 1.31 (t, 3H, J=7.6 Hz), 2.94 (q, 2H), J=7.6 Hz), 7.63 (dd, 1H, J=1.1, 8.4 Hz), 7.81 (d, 1H, J=8.4 Hz), 8.06 (d, 1H, J=1.1 Hz), 12.95 (br s, 1H); MS (Cl, $NH_3$) m/z 191 (M+H+, base); Anal. calcd for $C_{10}H_{10}N_2O_2$: C, 63.14; H, 5.30; N, 14.73. Found: C, 62.66; H, 5.42; N, 14.80.

EXAMPLE 6

3-1H-indazole-6-carboxylic acid methyl ester 8.78 g (45.8 mmol, 1.1 equiv) 1-(3-dimethylaminopropyl)-3-ethylcarbodiimide hydrochloride were added in one portion to a room temperature solution of 7.92 g (41.6 mmol, 1.0 equiv) 3-ethyl-1h-indazole-6-carboxylic acid, 16.9 mmol, 10 equiv) methanol and 5.59 g (45.8 mmol, 1.1 equiv) DMAP in 2560 mL $CH_2Cl_2$. After 18 h at room temperature, the reaction mixture was concentrated to ~150 mL, diluted with 500 mL ethyl acetate, washed 2×100 mL 1N HCl, 1×100 mL $H_2O$, 1×100 mL brine, and dried over $Na_2SO_4$. Filtration, concentration of filtrate and drying gave 7.8 g of brown solid, which was purified on a silica gel column (30% to 50% ethyl acetate/hexanes gradient) to give 6.41 g (75%) of a tan solid: mp 107–108° C.; IR (KBr) 3100–2950, 1723, 1222 cm$^{-1}$; $^1$NMR (300 MHz, CDCl$_3$) δ 8.19 (m, 1H, 7.7–7.8 (m, 2H), 3.96 (s, 3H), 3.05 (q, 2H, J=7.7 Hz), 1.43 (t, 3H, 7.7 Hz); MS (Cl, $NH_3$) m/z 205 (M+H+, base); Anal. calcd for $C_{11}H_{12}N_2O_2$: C, 64.70; H, 5.92; N, 13.96.

EXAMPLE 7

1-Cyclopentyl-3-ethyl-1H-indazole-6-carboxylic acid methyl ester 1.17 g (29.4 mmol, 1.05 equiv) sodium hydride, 60% oil dispersion, were added in one portion to a room temperature solution of 5.7 g (27.9 mmol, 1.0 equiv) 3-ethyl-1H-indazole-6-carboxylic acid methyl ester in 125 mL anhydrous DMF. After 20 min., 3.89 mL (36.6 mmol, 1.3 equiv) cyclopentyl bromide were added dropwise, and the reaction mixture allowed to stir overnight at room temperature. The mixture was then poured into 1 L $H_2O$ and extracted 3×450 mL ethyl acetate. The organic extracts were combined, washed 3×400 mL $H_2O$, 1×200 mL brine, and dried over $Na_2SO_4$. Filtration, concentration of filtrate and drying gave an amber oil, which was purified on a silica gel column (10% ethyl acetate/hexanes, gravity) to give 5.48 g (72%) of a clear oil: $^1$H NMR (300 MHz, CDCl$_3$) δ 8.16 (d, 1H, J=1.0 Hz), 7.7 (m, 2H), 5.00 (quintet, 1H, J=7.5 Hz), 3.97 (s, 3H), 3.01 (q, 2H, J=7.6 Hz), 2.2 (m, 4H), 2.0 (m, 2H), 1.8 (m, 2H), 1.39 (t, 3H, J=7.6 Hz); HRMS calcd for $C_{18}H_{20}N_2O_2$ 272.1526. Found: 272.15078.

EXAMPLE 8

1-Cyclopentyl-3-ethyl-1H-indazole-6-carboxylic acid

A mixture of 5.24 g (19.2 mmol, 1.0 equiv) 1-cyclopentyl-3-ethyl-1H-indazole-6-carboxylic acid methyl ester in 120 mL methanol and 60 mL 1N NaOH was heated to reflux. After 1h, the reaction mixture was cooled to room temperature, concentrated to 75 mL, acidified to pH=1 with 1N HCl, and extracted 2×200 mL ethyl acetate. The organic extracts were combined, washed 1×150 mL $H_2O$, 1×150 mL brine, and dried over $Na_2SO_4$. Filtration, concentration of filtrate and drying gave 4.79 g (96%) of a white solid. A small sample was recrystallized from ethyl acetate/hexanes to obtain analytical data: mp 157–159° C.; Ir (KBr) 3100–2500, 1683, 1298 cm$^{-1}$; $^1$H NMR (300 MHz, DMSO-$d_6$) δ 13.0 (br s, 1H, 8.21 (s, 1H), 7.79 (d, 1H, J=7.9 Hz), 7.62 (sdd, 1H, J=1.2, 8.4 Hz), 5.18 (quintet, 1H, J=7.5 Hz), 2.92 (q, 2H, J=7.6 Hz), 2.1 (m, 2H), 2.0 (m, 2H), 1.85 (m, 2H), 1.6 (m, 2H), 1.29 (t, 3H, J=7.6 Hz); MS (Cl, $NH_3$) m/z 259 (M+H+, base); Anal. calcd for $C_{15}H_{18}N_2O_2$: C,69.74; H, 7.02; N, 10.85. Found: C, 69.77; H, 7.02; N, 10.85.

EXAMPLE 9

1-Cyclopentyl-3-ethyl-1H-indazole-6-carboxylic acid (3,5-dicholoro-pyridin-4-yl)-amide 9.A 1-Cyclopentyl-3-ethyl-1H-indazole-6-carboxylic acid 7.73 mL (18.9 mmol, 1.0 equiv) n-butyl lithium, 2.45M in hexanes, were added dropwise to a −78° C. solution of 5.55 g (18.9 mmol, 1.0 equiv) 6-bromo-1-cyclopentyl-3-ethyl-1H-indazole in 100 mL anhydrous THF. After 30 minutes, $CO_2$ (g) was bubbled into the reaction mixture for 15 minutes. The reaction mixture was warmed to room temperature over several hours, then poured into 600 mL $H_2O$, acidified to pH=1, and extracted 2×250 mL ethyl acetate.

The organic extracts were combined, washed 1×150 mL H$_2$O, 1×100 mL brine, and dried over Na$_2$SO$_4$. Filtration, concentration of filtrate and drying gave 4.90 g (100%) of off-white crystals: mp 153–155° C.; $^1$H NMR (300 MHz, DMSO-d$_6$) identical with the spectrum of the product from Example 12.

9.B 1-Cyclopentyl-3-ethyl-1H-indazole-6-carbonyl chloride

791 μL (10.8 mmol, 1.4 equiv) thionyl chloride were added to a room temperature solution of 2.00 g (7.74 mmol, 1.0 equiv) 1-cyclopentyl-3-ethyl-1H-indazole-6-carboxylic acid and 100 μL DMF in 100 mL anhydrous toluene. The reaction mixture was heated to reflux for two hours, then cooled to room temperature, concentrated on a rotary evaporator, and dried at high vacuum, room temperature to give 2.16 g (100%) of brown crystals: mp 46–48° C.; MS (Cl, NH$_3$) m/z 279 (M+H$^+$, $^{37}$Cl), 277 (M+H$^+$, $^{35}$Cl).

9.C 1-Cyclopentyl-3-ethyl-1H-indazole-6-carboxylic acid (3,5-dichloro-pyridin-4-yl)-amide This compound was prepared according to the method of example 1.F, using 1.08 g (3.87 mmol) 1-cyclopentyl-3-ethyl-1H-indazole-6-carbonyl chloride as starting material, to give 1.327 g (85%) of pale yellow crystalline solid: mp 174–176° C.; MS (Cl, NH$_3$) m/z 405 (M+H$^+$, $^{37}$Cl), 403 (M+H$^+$, $^{35}$Cl); Anal. calcd for C$_{20}$H$_{20}$N$_4$OCl$_2$: C, 59.56; H, 5.00; N, 13.89. Found: C, 60.23; H, 5.42; N, 14.09.

EXAMPLE 10

1-Cyclopentyl-3-ethyl-1H-indazole-6-carboxylic acid (4,6-dichloro-pyrimidin-5-yl)-amide 50 μL (0.680 mmol, 1.3 equiv) thionyl chloride were added to a room temperature solution of 135 mg (0.523 mmol, 1.0 equiv) 1-cyclopentyl-3-ethyl-1h-indazole-6-carboxylic acid and 10 μL DMF in 5 mL anhydrous toluene. The reaction mixture was heated to reflux for 2 hours, then cooled to room temperature, concentrated to dryness on a rotary evaporator, and dried at high vacuum, room temperature for several hours. 21 mg (0.523 mmol, 1.0 equiv) sodium hydride, 60% oil dispersion, were added to a separate flask containing a room temperature solution of 86 mg (0.523 mmol, 1.0 equiv) 5-amino-4,6-dichloro-pyrimidine in 5 mL anhydrous DMF. After 10 minutes, a solution of the acid chloride (prepared above) in 5 mL anhydrous DMF was added, and the mixture stirred for 24 hours at room temperature. The reaction mixture was then heated to 70° C. for 1.5 hours, cooled to room temperature, diluted with 75 mL ethyl acetate, washed 2×15 mL H$_2$O, 1×16 mL brine, and dried over MgSO$_4$. The crude product was purified on a silica gel column (20 % ethyl acetate/hexanes) to give 31 mg (15%) of white crystalline solid: mp 171–172° C.; Anal. calcd for C$_{19}$H$_{19}$N$_5$OCl$_2$: C, 56.44; H, 4.74; N, 17.32. Found: C, 56.38; H, 4.76; N, 17.33.

EXAMPLE 11

1-Cyclopentyl-3-ethyl-1H-indazole-6-carboxylic acid phenylamide

46 μL (0.629 mmol, 1.3 equiv) thionyl chloride were added to room temperature solution of 125 mg (0.484 mmol, 1.0 equiv) 1-cyclopentyl-3-ethyl-1H-indazole-6-carboxylic acid and 5 μL DMF in 5 mL anhydrous toluene. The reaction mixture was heated to reflux for 2 h, then cooled to room temperature, concentrated to dryness on a rotary evaporator, and dried at high vacuum, room temperature for several hours. The crude acid chloride was dissolved in 5 mL CH$_2$Cl$_2$ and added to a room temperature solution of 49 μL (0.532 mmol, 1.1 equiv) aniline and 67 μL (0.484 mmol, 1.0 equiv) triethylamine in 5 mL CH$_2$Cl$_2$. After 18 h at room temperature, the reaction mixture was diluted with 75 mL ethyl acetate, washed 1×15 mL each 1N HCl, H$_2$O, brine, and dried over Na$_2$SO$_4$. Filtration, concentration of filtrate and drying gave 180 mg of an amber oil, which was purified on a silica gel column to give 160 mg of an off-white solid. Crystallization from ethyl acetate/hexanes gave 130 mg (81%) of a white crystalline solid: mp 146–147° C.; Anal. calcd for C$_{21}$H$_{23}$N$_3$O: C, 75.65; H, 6.95; N, 12.60. Found: C, 75.65; H, 7.03; N, 12.55.

EXAMPLE 12

4-[(1-Cyclopentyl-3-ethyl-1H-indazole-6-carbonyl)-amino]benzoic acid methyl ester This compound was prepared according to the method of Example 11, using 300 mg (1.16 mmol, 1.0 equiv) 1-cyclopentyl-3-ethyl-1H-indazole-6-carboxylic acid and 193 mg (1.28 mmol, 1.1 equiv) methyl-4-amino-benzoate as starting materials to give 415 mg (91%) of white crystals: mp 129–132° C.; Anal. calcd for C$_{23}$H$_{25}$N$_3$O$_3$: C, 70.56; H, 6.44; N, 10.73. Found: C, 70.36; H, 6.43; N, 10.61.

EXAMPLE 13

1-Cyclopentyl-3-ethyl-1H-indazole-6-carboxylic acid (3-chloro-phenyl)-amide

This compound was prepared according to the method of Example 11, using 150 mg (0.581 mmol, 1.0 equiv) 1-cyclopentyl-3-ethyl-1H-indazole-6-carboxylic acid and 68 μL (0.639 mmol, 1.1 equiv) 3-chloro-aniline as starting materials to give 211 mg (99%) of a clear oil; HRMS calcd for C$_{21}$H$_{22}$N$_3$OCl+H: 368.1532. Found: 368.1567.

EXAMPLE 14

1-Cyclopentyl-3-ethyl-1H-indazole-6-carboxylic acid(3-methoxy-phenyl)-amide 87 mg (0.708 mmol, 1.0 equiv) DMAP were added to a room temperature solution of 196 mg (0.708 mmol, 1.0 equiv) 1-cyclopentyl-3-ethyl-1H-indazole-6-carbonyl chloride, 99μL (0.708 mmol, 1.0 equiv) triethylamine and 80 μL (0.708 mmol, 1.0 equiv) m-anisidine in 5 mL CH$_2$Cl$_2$. After 48 hours, the reaction mixture was diluted with 75 mL ethyl acetate, washed 2×15 mL 1N HCl, 1×15 mL H$_2$O, 1×15 mL brine, and dried over MgSO$_4$. Filtration, concentration of filtrate and drying gave 0.27 g of an amber solid, which was purified by silica gel chromatography (ethyl acetate/hexanes gradient 10% (20%) to give 118 mg of a clear oil. Crystallization from petroleum ether gave 75 mg (29%) of a white powder: mp 91–93° C.; Anal. calcd for C$_{22}$H$_{25}$N$_3$O$_2$: C, 72.71; H, 6.95; N, 11.56. Found: C, 72.35; H, 7.15; N, 11.47.

EXAMPLE 15

1-Cyclopentyl-3-ethyl-1H-indazole-6-carboxylic acid pyridin-4-ylamide

46 μL (0.629 mmol, 1.3 equiv) thionyl chloride were added to a room temperature solution of 125 mg (0.484 mmol, 1.0 equiv) 1-cyclopentyl-3-ethyl-1H-indazole-6-carboxylic acid and 5 μL DMF in 5 mL anhydrous toluene. The reaction mixture was heated to reflux for 2 hours, then cooled to room temperature, concentrated to dryness on a rotary evaporator, and dried at high vacuum, room temperature for several hours. The crude acid chloride was dissolved in 5 mL anhydrous pyridine, 50 mg (0.532 mmol, 1.1 equiv) 4-aminopyridine were added, and the mixture heated to 40° C. for 1 hour. The reaction mixture was cooled to room temperature and allowed to stand overnight. 10 mL H$_2$O were added, and the mixture was concentrated to dryness on a rotary evaporator. The residue was taken up in 50 mL H$_2$O and 25 mL CH$_2$Cl$_2$, and the layers separated. The aqueous layer was extracted 1×25 mL CH$_2$Cl$_2$. The organic extracts were combined, washed 1×10 mL each H$_2$O, brine, and dried over Na$_2$SO$_4$. Filtration, concentration of filtrate and drying gave 133 mg of a white foam, which was purified on a silica gel column (25% CH$_3$OH/CH$_2$Cl$_2$) to give 122 mg of white needles. Recrystallization from ethyl acetate/hexanes gave 101 mg (62%) of white shiny plates: mp 144–146° C.; Anal. calcd for C$_{20}$H$_{22}$N$_4$O: C, 71.83; H, 6.63; N, 16.75. Found: C, 72.00; H, 7.03; N, 16.16.

EXAMPLE 16
1-Cyclopentyl-3-ethyl-1H-indazole-6-carboxylic acid pyridin-3-ylamide This compound was prepared according to the method of Example 15, using 58 mg (0.210 mmol, 1.0 equiv) 1-cyclopentyl-3-ethyl-1H-indazole-6-carbonyl chloride and 22 mg (0.231 mmol, 1.1 equiv) 3-aminopyridine as starting materials, to give 24 mg (34%) of white crystals: mp 133–135° C.; HRMS calcd for C$_{20}$H$_{22}$N$_4$O+H: 335:1872. Found: 335.1900.

EXAMPLE 17
1-Cyclopentyl-3-ethyl-1H-indazole-6-carboxylic acid pyridin-2-ylamide This compound was prepared according to the method of Example 15, using 49 mg (0.177 mmol, 1.0 equiv) 1-cyclopentyl-3-ethyl-1H-indazole-6-carbonyl chloride and 18 mg (0.195 mmol, 1.1 equiv) 2-aminopyridine as starting materials, to give 17 mg (34%) of yellow amorphous foam: HRMS calcd for C$_{20}$H$_{22}$N$_4$O+H: 335:1872. Found: 335.1874.

EXAMPLE 18
1-Cyclopentyl-3-ethyl-1H-indazole-6-carboxylic acid (pyridin-4-ylmethyl)-amide This compound was prepared according to the method of Example 15, using 51 mg (0.184 mmol, 1.0 equiv) 1-cyclopentyl-3-ethyl-1H-indazole-6-carbonyl chloride and 20 μL (0.193 mmol, 1.05 equiv) 4-(aminomethyl)pyridine as starting materials, to give 13 mg (20%) of white crystals: mp 147–149° C.; HRMS calcd for C$_{21}$H$_{24}$N$_4$O+H: 349.2028. Found: 349.2031.

EXAMPLE 19
1-Cyclopentyl-3-ethyl-1H-indazole-6-carboxylic acid(2-pyridin-4-yl-ethyl)-amide This compound was prepared according to the method of Example 15, using 78 mg (0.282 mmol, 1.0 equiv) 1-cyclopentyl-3-ethyl-1H-indazole-6-carbonyl chloride and 36 μL (0.295 mmol, 1.05 equiv) 4-(2-aminoethyl)pyridine as starting materials, to give 35 mg (35%) of white crystals: mp 123–126° C.; Anal. calcd for C$_{22}$H$_{26}$N$_4$O.¼H$_2$O: C, 72.01; H, 7.28; N, 15.27. Found: C, 71.77; H, 7.45; N, 15.23.

EXAMPLE 20
1-Cyclopentyl-3-ethyl-1H-indazole-6-carboxylic acid quinolin-5-ylamide This compound was prepared according to the method of Example 15, using 91 mg (0.329 mmol, 1.0 equiv) 1-cyclopentyl-3-ethyl-1H-indazole-6-carbonyl chloride and 52 mg (0.362 mmol, 1.1 equiv) 5-amino-quinoline as starting materials, to give 38 mg (30%) of pale yellow powder: mp 176–178° C.; Anal. calcd for C$_{24}$H$_{24}$N$_4$O: C, 74.96; H, 6.29; N, 14.57. Found: C, 74.33; H, 6.53; N, 14.31.

EXAMPLE 21
1-Cyclopentyl-3-ethyl-1H-indazole-6-carboxylicacid(2,6-dichloro-phenyl)-amide 1.1 mL (15.1 mmol, 1.3 equiv) thionyl chloride were added to a room temperature solution of 3.00 g (11.6 mmol, 1.0 equiv) 1-cyclopentyl-3-ethyl-1H-indazole-6-carboxylic acid and 150 μL DMF in 60 mL anhydrous toluene. The reaction mixture was heated to reflux for two hours, then cooled to room temperature, concentrated on a rotary evaporator, and dried at high vacuum, room temperature to give 3.40 g yellow-brown crystals. 1.88 g (11.6 mmol, 1.0 equiv) 2,6-dichloroaniline were added, and the mixture heated in a 200° C. oil bath under nitrogen atmosphere. After 15 minutes, the reaction mixture was cooled to room temperature. 75 mL ethyl acetate and 50 mL saturated aqueous NaHCO$_3$ were added, and the mixture stirred for 10 minutes. The layers were separated, and the organic layer was washed 1×20 mL saturated NaHCO$_3$, 1×10 mL H$_2$O, 1×20 mL brine, and dried over Na$_2$SO$_4$. Filtration, concentration of filtrate and drying gave a brown solid, which was recrystallized from ethyl acetate/hexanes to give 3.78 g (81%) of tan crystalline solid: mp 177–179° C.; Anal. calcd for C$_{21}$H$_{21}$N$_3$OCl$_2$: C, 62.69; H, 5.26; N, 10.45. Found: C, 62.67; H, 5.20; N, 10.43.

EXAMPLE 22
4-[(1-Cyclopentyl-3-ethyl-1H-indazole-6-carbonyl)-amino]-benzoic acid A mixture of 380 mg (0.971 mmol, 1.0 equiv) 4-[(1-cyclopentyl-3-ethyl-1H-indazole-6-carbonyl)-amino]-benzoic acid methyl ester, 4 mL 1N NaOH and 20 mL methanol was heated to reflux for 40 minutes. After cooling to room temperature, the reaction mixture was concentrated on a rotary evaporator, and the residue diluted with 150 mL H$_2$O, acidified to pH=1, and extracted 2×50 mL ethyl acetate. The organic extracts were combined, washed 1×25 mL each H$_2$O, brine, and dried over Na$_2$SO$_4$. Filtration, concentration of filtrate, and drying at high vacuum, room temperature gave 298 mg (81%) of a white crystalline solid: mp 249–251° C.; Anal. calcd for C$_{22}$H$_{23}$N$_3$O$_3$: C, 70.00; H, 6.14; N, 11.13. Found: C, 69.66; H, 6.13; N, 11.08.

EXAMPLE 23
1-Cyclopentyl-3-ethyl-1H-indazole-6-carboxylic acid (4-benzyloxycarbamoylphenyl)-amide 140 mg (0.728 mmol, 1.1 equiv) 1-(3-dimethylaminopropyl)-3-ethylcarbodiimide hydrochloride were added in one portion to a room temperature solution of 250 mg (0.662 mmol, 1.0 equiv) 4-[(1-cyclopentyl-3-ethyl-1H-indazole-6-carbonyl)-amino]-benzoic acid, 106 mg (0.662 mmol, 1.0 equiv) O-benzylhydroxylamine hydrochloride, 101 mg (0.662 mmol, 1.0 equiv) 1-hydroxybenzotriazole hydrate, and 194 μL (1.39 mmol, 2.1 equiv) triethylamine in 25 mL CH$_2$Cl$_2$. After 18 hours, the reaction mixture was diluted with 150 mL ethyl acetate, washed 1×25 mL each 1N HCl, H$_2$O, brine, and dried over Na$_2$SO$_4$. The crude product was purified on a silica gel column (2% CH$_3$OH/CH$_2$Cl$_2$, flash) to give 212 mg (66%) of white crystalline solid: mp 194–198° C.; Anal. calcd for C$_{28}$H$_{30}$N$_4$O$_3$: C, 72.17; H, 7.10; N, 11.61. Found: C, 71.62; H, 6.47; N, 11.85.

EXAMPLE 24
1-Cyclopentyl-3-ethyl-1H-indazole-6-carboxylic acid (4-hydroxycarbamoylphenyl)-amide A mixture of 187 mg (0.387 mmol, 1.0 equiv) 1-cyclopentyl-3-ethyl-1H-indazole-6-carboxylic acid (4-benzyloxycarbamoyl-phenyl)-amide and 200 mg 10% Pd/C in 10 mL ethyl acetate and 10 mL methanol was placed on a Parr® hydrogenation appartus and shaken under 30 psi H$_2$ at room temperature for 1 hour. The reaction mixture was filtered through Celite®, and the filtrate concentrated and dried to give a tan solid. Purification on a silica gel column (CH₃OH/CH₂Cl₂ gradient 4%, 10%, 20%, flash) gave 74 mg (49%) of a tan solid: mp 175° C. (dec); HRMS calcd for $C_{22}H_{24}N_4O_3$+H: 393.1928. Found: 393.1949.

EXAMPLE 25

25.A 1-Cyclobutyl-3-ethyl-1H-indazole-6-carboxylic acid methyl ester

This compound was prepared according to the method of Preparation 3, using 750 mg (3.67 mmol, 1.0 equiv) 3-ethyl-1H-indazole-6-carboxylic acid methyl ester and 0.38 mL (4.04 mmol, 1.1 equiv) cyclobutyl bromide as starting materials to give 307 mg (32%) of a clear oil: HRMS calcd for $C_{15}H_{18}N_2O_2$+H: 259.1447. Found: 259.14550.

25.B 3-Ethyl-1-isopropyl-1H-indazole-6-carboxylic acid methyl ester

This compound was prepared according to the method of Preparation 3, using 750 mg (3.67 mmol, 1.0 equiv) 3-ethyl-1H-indazole-6-carboxylic acid methyl ester and 0.38 mL (4.04 mmol, 1.1 equiv) 2-bromopropane as starting materials to give 359 mg (40%) of a clear oil: HRMS calcd for $C_{14}H_{18}N_2O_2$+H: 247.1448. Found: 247.14530.

25.C 1-Cyclopropylmethyl-3-ethyl-1H-indazole-6-carboxylic acid methyl ester

This compound was prepared according to the method of Preparation 3, using 750 mg (3.67 mmol, 1.0 equiv) 3-ethyl-1H-indazole-6-carboxylic acid methyl ester and 0.39 mL (4.04 mmol, 1.1 equiv) cyclopropylmethyl bromide as starting materials to give 338 mg (36%) of a clear oil: HRMS calcd for $C_{15}H_{18}N_2O_2$+H: 259:1447. Found 259.1435.

25.D 1-Cyclohex-2-enyl-3-ethyl-1H-indazole-6-carboxylic acid methyl ester

This compound was prepared according to the method of Preparation 1, using 750 mg (3.67 mmol, 1.0 equiv) 3-ethyl-1H-indazole-6-carboxylic acid methyl ester and 0.46 mL (4.04 mmol, 1.1 equiv) 3-bromocyclohexene as starting materials to give 467 mg (45%) of a clear oil: HRMS calcd for $C_{27}H_{20}N_2O_2$: 284.1525. Found: 284.1512.

25.E 3-Ethyl-1-[6-(4-phenyl-butoxy)-hexyl]-1H-indazole-6-carboxylic acid methyl ester This compound was prepared according to the method of Preparation 3, using 137 mg (0.671 mmol, 1.0 equiv) 3-ethyl-1H-indazole-6-carboxylic acid methyl ester and 273 mg (0.872 mmol, 1.3 equiv) 6-(4-phenyl-butoxy)-hexyl bromide as starting materials to give 163 mg (56%) of a yellow oil: HRMS calcd for $C_{27}H_{36}N_2O_3$+H: 437.2804. Found 437.2833.

EXAMPLE 26

26.A 1-Cyclobutyl-3-ethyl-1H-indazole-6-carboxylic acid

This compound was prepared according to the method of Preparation 3, using 225 mg (0.906 mmol, 1.0 equiv) 1-cyclobutyl-3-ethyl-1H-indazole-6-carboxylic acid methyl ester as starting material to give 168 mg (76%) of an off white crystalline solid: mp 148–150° C.; HRMS calcd for $C_{14}H_{16}N_2O_2$+H: 245.1290. Found: 245.1302.

26.B 3-Ethyl-1-isopropyl-1H-indazole-6-carboxylic acid

This compound was prepared according to the method of Preparation 3, using 300 mg (1.22 mmol. 1.0 equiv) 3-ethyl-1-isopropyl-1H-indazole-6-carboxylic acid methyl ester as starting material to give 260 mg (92%) of a pale yellow crystalline solid: mp 160–163° C.; Anal. calcd for $C_{13}H_{16}N_2O_2$: C, 67.21; H, 6.94; N, 12.05. Found: C, 67.07; H, 7.04; N, 12.16.

26.C 1-Cyclopropylmethyl-3-ethyl-1H-indazole-6-carboxylic acid

This compound was prepared according to the method of Preparation 3, using 294 mg (1.14 mmol, 1.0 equiv) 1-cyclopropylmethyl-3-ethyl-1H-indazole-6-carboxylic acid methyl ester as starting material to give 261 mg (94%) of a pale yellow crystalline solid: mp 126–130° C.; Anal. calcd for $C_{14}H_{16}N_2O_2$: C, 68.83; H, 6.60; N, 11.46. Found: C, 68.39; H, 6.67: N, 11.41.

26.D 3-Ethyl-1-[6-(4-phenyl-butoxy)phexyl]-1H-indazole-6-carboxylic acid

This compound was prepared according to the method of Preparation 3, using 147 mg (0.337 mmol, 1.0 equiv) 3-ethyl-1-[6-(4-phenyl-butoxy)-hexyl]-1H-indazole-6-carboxylic acid methyl ester as starting material to give 137 mg (96%) of a pale yellow oil: HRMS calcd for $C_{26}H_{34}N_2O_3$+H: 423.2648. Found. 423.26795.

EXAMPLE 27

27.A 1-Cyclohexyl-3-ethyl-1H-indazole-6-carboxylic acid methyl ester

A mixture of 417 mg (1.47 mmol, 1.0 equiv) 1-cyclohex-2-enyl-3-ethyl-1H-indazole-6-carboxylic acid methyl ester and 50 mg of 10% Pd/C, 50% water wet in 20 mL ethyl acetate was placed on a Parr® hydrogenation appartus and shaken under 45 psi $H_2$ for 45 minutes. The reaction mixture was filtered through Celite®, and the filtrate concentrated on a rotary evaporator and dried at high vacuum, room temperature to give 399 mg (95%) of a clear oil: HRMS calcd for $C_{17}H_{22}N_2O_2$+H: 287.1759. Found: 287.1783.

27.B 1-Cyclohexyl-3-ethyl-1H-indazole-6-carboxylic acid

This compound was prepared according to the method of Preparation 3, using 366 mg (1.28 mmol, 1.0 equiv) 1-cyclohexyl-3-ethyl-1H-indazole-6-carboxylic acid methyl ester as starting material to give 325 mg (93%) of a pale yellow solid: mp 196–197° C.; HRMS calcd for $C_{16}H_{20}N_2O_2$+H: 273.1603. Found: 273.1596.

EXAMPLE 28

28.A 3-Ethyl-1-(4-fluoro-phenyl)-1H-indazole-6-carboxylic acid methyl ester 0.245 mL (2.24 mmol, 2.0 equiv) 1-bromo-4-fluorobenzene were added to a room temperature suspension of 0.23 g (1.12 mmol, 1.0 equiv) 3-ethyl-1H-indazole-6-carboxylic acid methyl ester, 0.23 g (1.67 mmol, 1.5 equiv) potassium carbonate, and ~100 mg (0.348 mmol, 0.3 equiv) $Cu_2Br_2$ in 6 mL N-methylpyrrolidinone. The reaction mixture was heated to 175° C. for 28 hours, then cooled to room temperature, poured into 100 mL $H_2O$, and extracted 3×50 mL ethyl acetate. The organic extracts were combined, washed 2×50 mL $H_2O$, 1×50 mL brine. The aqueous washes were back extracted 1×75 mL with ethyl acetate. All ethyl acetate extracts were then combined and dried over $Na_2SO_4$. Filtration, concentration of filtrate and drying gave 0.6 g of brown oil, which was purified on a silica gel column (10% ethyl acetate/hexanes) to give 96 mg (29%) of a white crystalline solid: mp 72–74° C.; MS (Cl, $NH_3$) m/z 299 (M+H⁺, base).

28.B 3-Ethyl-1-(4-fluoro-phenyl)-1H-indazole-6-carboxylic acid

This compound was prepared according to the method of Preparation 3, using 96 mg (0.32 mmol, 1.0 equiv)3-ethyl-1-(4-fluoro-phenyl)-1H-indazole-6-carboxylic acid methyl ester as starting material to give 84 mg (92%) of a white solid: mp 204–205° C.; HRMS calcd for $C_{16}H_{13}N_2O_2F$+H: 285.1040. Found: 285.10257.

EXAMPLE 29

1-Cyclobutyl-3-ethyl-1H-indazole-6-carboxylic acid (3,5-dichloro-pyridin-4-yl)-amide This compound was prepared according to the method of Example 10, using 144 mg (0.589 mmol, 1.0 equiv) 1-cyclobutyl-3-ethyl-1H-indazole-6-carboxylic acid as

EXAMPLE 30
3-Ethyl-1-isopropyl-1H-indazole-6-carboxylic acid (3,5-dichloro-pyridin-4-yl)-amide This compound was prepared according to the method of Example 10, using 232 mg (1.00 mmol, 1.0 equiv) 3-ethyl-1-isopropyl-1H-indazole-6-carboxylic acid as starting material, to give 73 mg (20%) of an off white crystalline solid: mp 145–148° C.; HRMS calcd for $C_{18}H_{18}N_4OCl_2$+H: 377.0936. Found: 377.0938.

EXAMPLE 31
1-Cyclopropylmethyl-3-ethyl-1H-indazole-6-carboxylic acid (3,5-dichloropyridin-4-yl)-amide This compound was prepared according to the method of Example 10, using 224 mg (0.917 mmol, 1.0 equiv) 1-cyclopropylmethyl-3-ethyl-1-H-indazole-6-carboxylic acid as starting material, to give 51 mg (14%) of an off white crystalline solid: mp 148–150° C.; HRMS calcd for $C_{19}H_{18}N_4OCl_2$+H:389.0936. Found: 389.091.

EXAMPLE 32
1-Cyclohexyl-3-ethyl-1H-indazole-6-carboxylic acid (3,5-dichloro-pyridin-4-yl)-amide This compound was prepared according to the method of Example 10, using 300 mg (1.10 mmol, 1.0 equiv) 1-cyclohexyl-3-ethyl-1H-indazole-6-carboxylic acid as starting material, to give 83 mg (18%) of an off white crystalline solid: mp 124–127° C.; MS(Cl, $NH_3$) m/z 421 ($M+H_+$, $_{37}Cl+_{37}Cl$), 419($M+H_m$, $_{35}Cl+_{37}Cl$, base), 417 ($M+H_+$, $_{35}Cl+C_{35}Cl$).

EXAMPLE 33
3-Ethyl-1-[6-(4-phenyl-butoxy)-hexyl]-1H-indazol-6-carboxylic acid (3,5-dichloro-pyridin-4-yl)-amide This compound was prepared according to the method of Example 1, using 127 mg (0.301 mmol, 1.0 equiv) 3-ethyl-1-[6-(4-phenyl-butoxy)-hexyl]-1H-indazole-6-carboxylic acid as starting material, to give 199 mg (70%) of a clear oil, which was crystallized from ether/hexanes to give 72 mg (42%) of white crystals: mp 76–79° C.; HRMS calcd for $C_{31}H_{36}N_4O_2Cl_2$+H:567.2294. Found: 567.2288.

EXAMPLE 34
3-Ethyl-1-(4-fluoro-phenyl)-1H-indazole-6-carboxylic acid (3,5-dichloro-pyridin-4-yl)-amide This compound was prepared according to the method of Example 10,using 80 mg (0.281 mmol, 10 equiv) 3-ethyl-1-(4-fluoro-phenyl)-1H-indazole-6-carboxylic acid as starting material, to give 22 mg (18%) of a white crystalline solid: mp 197–199° C.; HRMS calcd for $C_{21}H_{15}N_4OCl_2F$+H: 429.0688. Found: 429.0704.

EXAMPLE 35
[(1-Cyclopentyl-3-ethyl-1H-indazole-6-carbonyl)-amino]-acetic acidmethylester 134 mg (0.697 mmol, 1.0 equiv) 1-(3-dimethylaminopropyl)-3-ethylcarbodiimide hydrochloride were added in one portion to a room temperature solution of 180 mg (0.697 mmol, 1.0 equiv) 1-cyclopentyl-3-ethyl-1H-indazole-6-carboxylic acid, 87.5 mg (0.697 mmol, 1.0 equiv) glycine methyl ester hydrochloride, 107 mg (0.697 mmol, 1.0 equiv) 1-hydroxybenzotriazole hydrate, and 194 μL (1.39 mmol, 2.0 equiv) triethylamine in 5 mL $CH_2Cl_2$. After 18 h, the reaction mixture was diluted with 150 mL ethyl acetate, washed 1×25 mL each 1N HCl, $H_2O$, brine, and dried over $Na_2SO_4$. The crude product was purified on a silica gel column (40% ethyl acetate/hexanes, flash) to give 187 mg (66%) of a white waxy solid: mp 89–93° C.; Anal. calcd for $C_{18}H_{23}N_3O_3$; C, 65.63; H, 7.04; N, 12.76. Found: C, 65.74; H, 7.02; N, 12.74.

EXAMPLE 36
[(1-Cyclopentyl-3-ethyl-1H-indazole-6-carbonyl)-amino]-acetic acid This compound was prepared according to the method of Preparation 3, using 170 mg (0.516 mmol, 1.0 equiv) [(1-cyclopentyl-3-ethyl-1H-indazole-6-carbonyl)-amino]-acetic acid methyl ester as starting material to give 155 mg (95%) white crystals: mp 182–184° C.; Anal. calcd for $C_{17}H_{21}N_3O_3$: C, 64.73; H, 6.71; N, 13.32. Found: C, 64.73; H, 6.80; N, 12.81.

EXAMPLE 37
1-Cyclopentyl-3-ethyl-1H-indazole-6-carboxylic acid (benzyloxycarbamoylmethyl)-amide This compound was prepared according to the method of Example 23, using 144 mg (0.457 mmol, 1.0 equiv) [(1-cyclopentyl-3-ethyl-1H-indazole-6-carbonyl)-amino]-acetic acid as starting material to give 125 mg (65%) of a white amorphous solid: $^1$H NMR (300 MHz, $CDCl_3$, partial) δ 493 (s, 2H), 3.00 (q, 2H, J=7.6 Hz), 2.2 (m, 4H), 2.0 (m, 2H), 1.7 (m, 2H), 1.39 (t, 3H, J=7.6 Hz); MS (Cl, $NH_3$) m/z 421 ($M+H_4$, base).

EXAMPLE 38
1-Cyclopentyl-3-ethyl-1H-indazole-6-carboxylic acid hydroxycarbamoylmethyl-amide A mixture of 120 mg (0.285 mmol, 1.0 equiv) 1-cyclopentyl-3-ethyl-1H-indazole-6-carboxylic acid (benzyloxycarbamoyl-methyl)-amide and 0.08 g 10% Pd/C, 50% water wet, in 10 mL methanol and 10 mL ethyl acetate was placed on a Parr® hydrogenation apparatus and shaken under 30 psi $H_2$ at room temperature for 40 minutes. The reaction mixture was filtered through Celite®, and the filtrate concentrated and dried to give 104 mg of a tan solid. Trituration with hexanes gave 69 mg (73%) of a tan crystalline powder: mp 105° C. (dec); HRMS calcd for $C_{17}H_{22}N_4O_3$+H: 331.1772. Found: 331.1769.

EXAMPLE 39
1-Cyclopentyl-3-ethyl-1H-indazole-6-carboxylic acid (2-methylsulfanyl-ethyl)-amide This compound was prepared according to the method of Example 35, using 57 mg (0.221 mmol, 1.0 equiv) 1-cyclopentyl-3-ethyl-1H-indazole-6-carboxylic acid and 20 mg (0.221 mmol, 1.0 equiv) 2-(methylthio)ethylamine as starting materials. Silica gel chromatography (30% ethyl acetate/hexanes) gave 53 mg (73%) of white crystals: mp 81–83° C.; Anal. calcd for $C_{18}H_{25}N_3O_8$: C, 65.21; H, 7.60; N, 12.68. Found: C, 65.26; H, 7.49; N, 12.81.

EXAMPLE 40
1-Cyclopentyl-3-ethyl-1H-indazole-6-carboxylic acid (methoxycarbamoyl-methyl)-amide This compound was prepared according to the method of Example 37, using 222 mg (0.704 mmol, 1.0 equiv)[(1-cyclopentyl-3-ethyl-1H-indazole-6-carbonyl)-amino]-acetic acid and 59 mg (0.704 mmol, 1.0 equiv) methoxylamine hydrochloride as starting materials to give 39 mg of a clear oil, which was crystallized from ether/hexanes to give 34 mg (14%) of white crystals: mp 135–136° C.; Anal. calcd for $C_{18}H_{24}N_4O_3$: C, 62.77; H, 7.02; N, 16.27. Found: C, 62.64; H, 6.87; N, 16.47.

EXAMPLE 41
3-[(1-Cyclopentyl-3-ethyl-1H-indazole-6-carbonyl)-amino]-propionic acid ethyl ester This compound was prepared according to the method of Example 35, using 297 mg (1.15 mmol, 1.0 equiv) 1-cyclopentyl-3-ethyl-1H-indazole-6-carboxylic acid and 177 mg (1.15 mmol, 1.0 equiv) beta-alanine ethyl ester hydrochloride as starting materials to give 372 mg (90%) of white crystals: mp 74–76° C.; Anal. calcd for $C_{20}H_{27}N_3O_3$: C, 67.21; H, 7.61; N, 11.76. Found: C, 67.40; H, 7.56; N, 11.99.

EXAMPLE 42
3-[(1-Cyclopentyl-3-ethyl-1H-indazole-6-carbonyl)-amino]-propionic acid A mixture of 330 mg (0.923 mmol, 1.0 equiv) 3-[(1-cyclopentyl-3-ethyl-1H-indazole-6-carbonyl)-amino]-propionic acid ethyl ester in 10 mL ethanol and 4 mL 1N NaOH was heated to reflux for 1 h. After cooling to room temperature, the reaction mixture was concentrated, diluted with 75 mL $H_2O$, acidified to pH 1, and extracted 3×35 mL ethyl acetate. The organic extracts were combined, washed 1×25 mL $H_2O$, 1×25 mL brine, and dried over $Na_2SO_4$. Filtration, concentration of filtrate on a rotary evaporator and drying at high vacuum, room temperature gave 297 mg (98%) of white solid: mp 151–153° C.; Anal. calcd for $C_{18}H_{23}N_3O_3$: C, 65.63; H, 7.04; N, 12.76. Found: C, 65.75; H, 7.12; N, 12.91.

EXAMPLE 43
1-Cyclopentyl-3-ethyl-1H-indazole-6-carboxylic acid (2-benzyloxycarbamoyl-ethyl)-amide This compound was prepared according to the method of Example 37, using 250 mg (0.759 mmol, 1.0 equiv) 3-[(1-cyclopentyl-3-ethyl-1H-indazole-6-carbonyl)-amino]-propionic acid and 121 mg (0.759 mmol, 1.0 equiv) O-benzylhydroxylamine hydrochloride as starting materials, to give 237 mg (72%) of a white solid: mp 134–136° C.; Anal. calcd for $C_{25}H_{30}N_4O_3$: C, 69.10; H, 6.96; N, 12.89. Found: C, 69.36; H, 6.75; N, 12.85.

EXAMPLE 44
1-Cyclopentyl-3-ethyl-1H-indazole-6-carboxylic acid (2-hydroxycarbamoyl-ethyl)-amide This compound was prepared according to the method of Example 38, using 203 mg (0.467 mmol, 1.0 equiv) 1-cyclopentyl-3-ethyl-1H-indazole-6-carboxylic acid (2-benzyloxycarbamoyl-ethyl)-amide as starting material and 50 mg of $Pd(OH)_2/C$ (Pearlman's catalyst) as catalyst, to give 147 mg (91%) of a white powder: mp 166–169° C.; Anal. calcd for $C_{18}H_{24}N_4O_3$: C, 62.77;H, 7.02; N, 16.27. Found: C, 62.58; H, 7.12; N, 16.27.

EXAMPLE 45
[(1-Cyclopentyl-3-ethyl-1H-indazole-6-carbonyl)-methyl-amino]-acetic acidethyl ester This compound was prepared according to the method of Example 35, using 284 mg (1.10 mmol, 1.0 equiv) 1-cyclopentyl-3-ethyl-1H-indazole-6-carboxylic acid and 169 mg (1.10 mmol, 1.0 equiv) sarcosine ethyl ester hydrochloride as starting materials, to give 220 mg (56%) of a clear oil: Anal. calcd for $C_{20}H_{27}N_3O_3$: C, 67.21; H, 7.61; N, 11.76. Found: C, 66.93; H, 7.73; N, 11.77.

EXAMPLE 46
[1-Cyclopentyl-3-ethyl-1H-indazole-6-carbonyl)-methyl-amino]-acetic acid.

This compound was prepared according to the method of Example 42, using 201 mg(0.562 mmol, 1.0 equiv)[(1-cyclopentyl-3-ethyl-1H-indazole-6-carbonyl)-methyl-amino]-acetic acid ethyl ester as starting material, to give 185 mg (100%) of a white amorphous solid: Anal. calcd for $C_{18}H_{23}N_3O_3$. $¼H_2O$: C, 64.74; H, 7.09; N, 12.58. Found: C, 64.73; H, 7.55; N, 12.47.

EXAMPLE 47
1-Cyclopentyl-3-ethyl-1H-indazole-6-carboxylic acid (benzyloxycarbamoyl-methyl)-methyl amide This compound was prepared according to the method of Example 37, using 160 mg (0.486 mmol, 1.0 equiv)[(1-cyclopentyl-3-ethyl-1H-indazole-6-carbonyl)-methyl-amino]-acetic acid as starting material, to give 134 mg (64%) of a clear oil: HRMS calcd for $C_2H_{30}N_4O_3$+H: 435.2398. Found: 435.2376.

EXAMPLE 48
1-Cyclopentyl-3-ethyl-1H-indazole-6carboxylic acid hydroxycarbamoylmethyl-methyl amide This compound was prepared according to the method of Example 38, using 126 mg (0.290 mmol, 1.0 equiv) 1cyclopentyl-3ethyl-1H-indazole-6-carboxylic acid (benzyloxycarbamoyl-methyl)-methyl amide as starting material and 40 mg of $Pd(OH)_2/C$ (Pearlman's catalyst) as catalyst, to give 78 mg (78%) of a light tan powder: mp 63° C. (dec); HRMS calcd for $C_{18}H_{24}N_4O_3$+H: 345,19285. Found: 345.1912.

EXAMPLE 49
1-Cyclopentyl-3-ethyl-1H-indazole-6-carboxylic acid [(hydroxy-methyl-carbamoyl)-methyl]-amide.

390 mg (16.9 mmol, 20 equiv) sodium, 3 to 8 mm spheres, were added to 10 mL of methanol portion wise for 30 minutes. A solution of 707 mg (8.47 mmol, 10 equiv) N-methylhydroxylamine hydrochloride in 10 mL methanol was added dropwise, and the reaction mixture allowed to stir 10 min. A solution of 279 mg (0.847 mmol, 1.0 equiv) [(1-cyclopentyl-3-ethyl-1H-indazole-6-carbonyl)-amino]-acetic acid methyl ester in 10 mL methanol was added drop wise, and the reaction allowed to stir 16 h at room temperature. The mixture was then concentrated to ½ of its initial volume, diluted with 150 mL $H_2O$, acidified to pH=2, and extracted 2×50 mL ethyl acetate. The organic extracts were combined, washed in 2×20 mL, $H_2O$ 1×20 mL brine, and dried over $Na_2SO_4$. Filtration, concentration of filtrate and drying gave 0.33 g of a clear oil, which was purified on a silica gel column (10% $CH_3OH/CH_2CL_2$, flash) to give 236 mg of a white foam. Trituration with pentane yielded 150 mg (51%) white amorphous solid; mp 60° C. (dec); Anal. calcd for $C_{18}H_{24}N_4O_3.H_2O$; 59.65; H, 7.23; N, 15.46. Found: C, 62.04; H, 7.39; N, 15,86.

EXAMPLE 50
50.A. S-(1-Benzyloxycarbamoyl-ethyl)-carbamic acid tert-butyl ester.

This compound was prepared according to the method of Example 44, using 500 mg (2.64 mmol, 1.0 equiv) N-(tert-butoxycarbonyl)-L-alanine and 422 mg (2.64 mmol, 1.0 equiv) O-benzylhydroxylamine hydrochloride, to give 583 mg (75%) of a white oily solid: $^1H$ NMR (300 MHz, $CDCl_3$) δ 9.02 (br s, 1H), 7.37 (m, 5H), 4.95 (m, 1H), 4.90 (s, 2H), 4.03 (m, 1H), 1.41 (s, 9H), 1.33 (d, 3H, J=7.0 Hz); MS (Cl, $NH_3$) m/z295(M+H$^+$, base).

50.B. S-2-Amino-N-benzyloxy-proprionamide hydrochloride.

HCl (g) was bubbled into a 0° C. solution of 561 mg (1.91 mmol, 1.0 equiv) S-(1-benzyloxycarbamoyl-ethyl)-carbamic acid tert-butyl ester in 10 mL anhydrous 1,4- dioxane over 1–2 minutes. The reaction mixture was allowed to stir at room temperature for 45 min., then was concentrated on a rotary evaporator and dried at high vacuum, room temperature to give 492 mg (>100%) white hygroscopic amorphous solid: $^1$H NMR (300 MHz, DMSO-$d_6$) δ 11.8 (s, 1H), 8.38 (br s, 3H), 7.38 (m, 5H), 4.82(m, 2H), 3.68 (m, 1H), 1.29 (d, 3H, J=6.9 Hz).

EXAMPLE 51

S-1-Cyclopentyl-3-ethyl-1H-indazole-6-carboxylic acid (1-benzyloxycarbamoyl-ethyl)-amide This compound was prepared according to the method of Example 37, using 200 mg (0.774 mmol, 1.0 equiv) 1-cyclopentyl-3-ethyl-1H-indazole-6-carboxylic acid and 180 mg (0.774 mmol, 1.0 equiv) S-2-amino-N-benzyloxy-propionamide hydrochloride as starting materials, to give 322 mg (96%) of a clear oil: HRMS calcd for $C_{25}H_{30}N_4O_3$+H: 435.2396. Found: 435:2424.

EXAMPLE 52

S-1-Cyclopentyl-3-ethyl-1H-indazole-6-carboxylic acid (1-hydroxycarbamoyl-ethyl)-amide This compound was prepared according to the method of Example 38, using 288 mg (0.663 mmol, 1.0 equiv) S-1-cyclopentyl-3-ethyl-1H-indazole-6-carboxylic acid (1-benzyloxycarbamoyl-ethyl)-amide as starting material and 90 mg Pd(OH)$_2$/C as catalyst, to give 170 mg (75%) tan powder: mp 106° C. (dec); HRMS calcd for $C_{18}H_{24}N_4O_3$+H: 345.1927. Found: 345.1923.

EXAMPLE 53

R-(1-Benzyloxycarbamoyl-ethyl)-carbamic acid tert-butyl ester.

This compound was prepared according to the method of Example 37, using 500 mg (2.64 mmol, 1.0 equiv) N-(tert-butoxycarbonyl)-D-alanine and 422 mg (2.64 mmol, 1.0 equiv) O-benzylhydroxylamine hydrochloride, to give 592 mg (76%) of a white oily solid: $^1$H NMR (300 MHz, CDCl$_3$) δ 9.02 (br s, 1H), 7.37 (m, 5H), 4.95 (m, 1H), 4.90 (s, 2H), 4.03 (m, 1H), 1.41 (s, 9H), 1.33 (d, 3H, J=7.0 Hz); MS (Cl, NH$_3$) m/z295 (M+H$^+$, base).

EXAMPLE 54

R-1-Cyclopentyl-3-ethyl-1H-indazole-6-carboxylic acid (1-hydroxycarbamoyl-ethyl)-amide 54.A. R-2- Amino-N-benzyloxy-propionamide hydrochloride.

HCl (g) was bubbled into a 0° C. solution of 570 mg (1.94 mmol, 1.0 equiv) R-(1-benzyloxycarbamoyl-ethyl)-carbamic acid tert-butyl ester in 10 mL anhydrous 1,4-dioxane over 1–2 minutes. The reaction mixture was allowed to stir at room temperature for 45 min., then was concentrated on a rotary evaporator and dried at high vacuum, room temperature to give 512 mg (>100%) white hygroscopic amorphous solid: $^1$H NMR (300 MHz, DMSO-$d_6$) δ 11.8 (s, 1H), 8.38 (br s, 3H), 7.38 (m, 5H), 4.82(m, 2H), 3.68 (m, 1H), 1.29 (d, 3H, J=6.9 Hz).

54.B. R-1-Cyclopentyl-3-ethyl-1H-indazole-6-carboxylic acid (1-benzyloxycarbamoyl-ethyl)-amide This compound was prepared according to the method of Example 37, using 200 mg (0.774 mmol, 1.0 equiv) 1-cyclopentyl-3-ethyl-1H-indazole-6-carboxylic acid and 180 mg (0.774 mmol, 1.0 equiv) R-2-amino-N-benzyloxy-propionamide hydrochloride as starting materials, to give 330 mg (98%) of a clear oil: HRMS calcd for $C_{25}H_{30}N_4O_3$+H: 435.2396. Found: 435.2414.

54.C. R-1-Cyclopentyl-3-ethyl-1H-indazole-6-carboxylic acid (1-hydroxycarbamoyl-ethyl)-amide This compound was prepared according to the method of Example 30, using 295 mg (0.679 mmol, 1.0 equiv) R-1-cyclopentyl-3-ethyl-1H-indazole-6-carboxylic acid (1-benzyloxycarbamoyl-ethyl)-amide as starting material and 90 mg Pd(OH)$_2$/C as catalyst, to give 201 mg (86%) tan powder: mp 102° C. (dec); HRMS calcd for $C_{18}H_{24}N_4O_3$+H: 345.1927. Found: 345.1927.

EXAMPLE 55

1-Cyclopentyl-3-ethyl-6-thiophen-2-yl-1H-indazole

A solution of 76 mg (0.598 mmol, 1.2 equiv) thiophene-2-boronic acid in 0.5 mL methanol was added to a room temperature suspension of 146 mg (0.498 mmol, 1.0 equiv) 6-bromo-1-cyclopentyl-3-ethyl-1H-indazole and 17 mg (0.0149 mmol, 0.03 equiv) Pd(PPh$_3$)$_4$in 2 mL toluene and 0.5 mL 2M aqueous Na$_2$CO$_3$. The mixture was heated to reflux for 4 h, then cooled to room temperature. The reaction mixture was diluted with 50 mL ethyl acetate, washed 1×10 mL each H$_2$O, brine, and dried over MgSO$_4$. The crude product was purified on a silica gel column (3% ethylacetate/hexanes, flash) to give 81 mg (55%) of a clear oil, which crystalized onstanding: mp 60–64° C.; HRMS calcd for $C_{18}H_{20}N_2S$+H: 297.1427. Found: 297.1484.

EXAMPLE 56

1-Cyclopentyl-3-ethyl-6-phenyl-1H-indazole

This compound was prepared according to the method of Example 55, using 128 mg (0.437 mmol, 1.0 equiv) 6-bromo-1-cyclopentyl-3-ethyl-1H-indazole and 75 mg (0.612 mmol, 1.4 equiv) phenyl boronic acid as starting materials, to give 98 mg (77%) of white crystals: mp 72–74° C.; Anal. calcd for $C_{20}H_{22}N_2$: C, 82.77; H, 7.64; N, 9.65. Found: C, 81.95; H, 7.82; N, 9.75.

EXAMPLE 57

1-Cyclopentyl-3-ethyl-1H-indazole-6-carboxylic acid (3,5-dichloro-pyridin-4-yl)-methyl-amide 5.2 mg (0.130 mmol, 1.05 equiv) sodium hybride, 60% oil dispersion, were added to a room temperature solution of 50 mg (0.124 mmol, 1.0 equiv) 1-cyclopentyl-3-ethyl-1H-indazole-6-carboxylic acid (3,5-dichlor-pyridin-4-yl)-amide in 3 mL anhydrous DMF. After 30 min. 7.7 μl (0.124 mmol, 1.0 equiv) iodomethane were added and the mixture stirred at room temperature for 4 h. The reaction mixture was diluted with 50 mL H$_2$O and extracted 2×20 mL ethyl acetate. The ethyl acetate extracts were combined, washed 2×5 mL H$_2$O, 1×5 mL brine, and dried over Na$_2$SO$_4$. Filtration, concentration of filtrate and drying gave a yellow oil, which was purified on a silica gel column (25% ethylacetate/hexanes, flash) to give 27 mg (52%) of a white crystalline solid: mp 118–119° C.; HRMS calcd for $C_{21}H_{22}N_4OCl_3$+H: 417.12519. Found: 417.12270.

EXAMPLE 58

1-Cyclopentyl-3-ethyl-1H-indazone-carboxylic acid dimethyl amide 47 mg (0.246 mmol, 1.1. equiv) of 1-(3-dimethylaminopropyl)-3-ethylcarbodiimide hydrochloride were added in one portion to a room temperature solution of 57.8 mg (0.224 mmoles, 1.0 equiv) 1-cyclopentyl-3-ethyl-1H-indazole-6-carboxylic acid, 18 mg (0.224 mmole, 1.0 equiv) dimethylamine hydrochloride, 34 mg (0.224 mmol, 1.0 equiv) hydroxybenzotrizole hydrate and 66 μl (0.470 mmol, 2.1 equiv) of triethylamine in 5.0 mL of anhydrous methylene chloride. After stirring the reaction mixture for 18 hours under a N$_2$ atmosphere, the reaction mixture was diluted with 40 mL of ethylacetate, washed with 10 mL of 1N HCl, water, and brine, and dried over $Na_2SO_4$. The crude product was purified on a silica gel column (50% EtOAc/50% $CH_2Cl_2$) to give 55 mg (86%) of clear oil: HRMS calcd for $C_{17}H_{23}N_3O+H$: 285.1843. Found: 285.1841.

What is claimed is:

1. A compound of the formula I

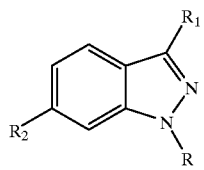

or a pharmaceutically acceptable salt thereof, wherein:

R is $C_1$–$C_9$ cycloalkyl, wherein said R group is optionally substituted by 1 to 3 substituents independently selected from the group consisting of halo, hydroxy, $C_1$–$C_5$ alkyl, $C_2$–$C_5$ alkenyl, $C_1$–$C_6$ alkoxy, trifluoromethyl, nitro, —$CO_2R_{12}$, —$C(O)NR_{12}R_{13}$, —$NR_{12}R_{13}$ and —$SO_2NR_{12}R_{13}$; where $R_{12}$ and $R_{13}$ are independently H or methyl;

$R_1$ is $C_1$–$C_9$ alkyl, wherein said $R_1$ group is optionally substituted by 1 to 3 substituents independently selected from the group consisting of methyl, ethyl, trifluoromethyl, and halo;

$R_2$ is —$Z_3$—$R_7$; where:

$Z_3$ is —$C(Y_1)NR_8(CHR_{12})_n$—, or —$NR_8C(Y_1)(CHR_{12})_n$—, where $Y_1$ is O, $R_8$ is H, $R_{12}$ is H, and n is 0 or 1; and $R_7$ is phenyl or pyridyl, each optionally substituted by 1 to 3 substituents independently selected from the group consisting of halo, trifluoromethyl, nitro, cyano, —$CO_2R_{12}$ where $R_{12}$ is H or methyl, —OC(O)($C_1$–$C_4$ alkyl), —$C(O)NH_2$, $C_1$–$C_4$ alkyl, and $C_1$–$C_4$ alkoxy.

2. The compound of claim 1 wherein $R_7$ is 2,6-dihalo-substituted phenyl, or 3,5-dihalo-pyrid-4-yl.

3. The compound of claim 1 wherein —$R_7$ is phenyl or pyridyl substituted by 1 to 3 substituents independently selected from —$CO_2CH_3$, methyl, methoxy, and —$C(O)NH_2$.

4. The compound of claim 1 wherein $R_7$ is phenyl or pyridyl substituted by 1 to 3 substituents independently selected from cyano, carboxy and —OC(O)($C_1$–$C_4$ alkyl).

5. The compound of claim 1 selected from the group consisting of

1-Cyclopentyl-3-ethyl-1H-indazole-6-carboxylic acid (3,5-dichloro-pyridin-4-yl)-amide;

1-Cyclopentyl-3-ethyl-1H-indazole-6-carboxylic acid (2,6-dichloro-phenyl)-amide;

1-Cyclobutyl-3-ethyl-1H-indazole-6-carboxylic acid (3,5-dichloro-pyridin-4-yl)-amide;

1-Cyclohexyl-3-ethyl-1H-indazole-6-carboxylic acid (3,5-dichloro-pyridin-4-yl)-amide;

1-Cyclopentyl-3-ethyl-1H-indazole-6-carboxylic acid hydroxycarbamoylmethyl-amide;

1-Cyclopentyl-3-ethyl-1H-indazole-6-carboxylic acid (2-methylsulfanyl-ethyl)-amide;

1-Cyclopentyl-3-ethyl-1H-indazole-6-carboxylic acid hydroxycarbamoylmethyl-methyl amide;

S-1-Cyclopentyl-3-ethyl-1H-indazole-6-carboxylic acid (1-benzyloxycarbamoyl-ethyl)-amide;

R-1-Cyclopentyl-3-ethyl-1H-indazole-6-carboxylic acid (1-hydroxycarbamoyl-ethyl)-amide; and the pharmaceutically acceptable salts of the foregoing compounds.

6. A pharmaceutical composition for the inhibition of phosphodiesterase (PDE) type IV or the production of tumor necrosis factor (TNF) in a mammal comprising a therapeutically-effective amount of the compound of claim 1 and a pharmaceutically acceptable carrier.

7. A method for the inhibition of phosphodiesterase (PDE) type IV or the production of 9249 tumor necrosis factor (TNF) in a mammal which comprises administering to said mammal a therapeutically-effective amount of the compound of claim 1.

8. A pharmaceutical composition for the prevention or treatment of asthma, acute respiratory distress syndrome, chronic pulmonary inflammatory disease, silicosis, pulmonary sarcoidosis, acquired immune deficiency syndrom (AIDS), AIDS, HIV, ARC (AIDS related complex), keloid formation, scar tissue formation, Crohn's disease, ulcerative colitis, pyresis, multiple sclerosis, bronchitis, chronic obstructive airway disease, or allergic rhinitis in a mammal, comprising a therapeutically-effective amount of the compound of claim 1 and a pharmaceutically acceptable carrier.

9. A method for treating asthma, acute respiratory distress syndrome, chronic pulmonary inflammatory disease, silicosis, pulmonary sarcoidosis, bronchitis, chronic obstructive airway disease, or allergic rhinitis in a mammal which comprises administering to said mammal a therapeutically-effective amount of the compound of claim 1.

* * * * *